US012685881B2

(12) United States Patent
Berube et al.

(10) Patent No.: US 12,685,881 B2
(45) Date of Patent: Jul. 21, 2026

(54) VECTOR TIGHTENING

(71) Applicant: Sofwave Medical Ltd., Yokneam Illit (IL)

(72) Inventors: Dany Berube, Milpitas, CA (US); Shimon Eckhouse, Haifa (IL)

(73) Assignee: Softwave Medical Ltd., Yokneam Illit (IL)

( * ) Notice: Subject to any disclaimer, the term of this patent is extended or adjusted under 35 U.S.C. 154(b) by 0 days.

(21) Appl. No.: 18/711,892

(22) PCT Filed: Nov. 22, 2022

(86) PCT No.: PCT/IL2022/051243
§ 371 (c)(1),
(2) Date: May 21, 2024

(87) PCT Pub. No.: WO2023/089625
PCT Pub. Date: May 25, 2023

(65) Prior Publication Data
US 2025/0001216 A1 Jan. 2, 2025

Related U.S. Application Data

(60) Provisional application No. 63/281,802, filed on Nov. 22, 2021.

(51) Int. Cl.
A61N 7/00 (2006.01)
(52) U.S. Cl.
CPC ........ A61N 7/00 (2013.01); *A61N 2007/0034* (2013.01)
(58) Field of Classification Search
CPC ........................... A61N 7/00; A61N 2007/0034
See application file for complete search history.

(56) References Cited

U.S. PATENT DOCUMENTS

| | | | |
|---|---|---|---|
| 4,800,316 A | 1/1989 | Ju-Zhen | |
| 5,620,479 A | 4/1997 | Diederich | |
| | | (Continued) | |

FOREIGN PATENT DOCUMENTS

| | | |
|---|---|---|
| CN | 1430538 | 7/2003 |
| CN | 101166472 | 4/2008 |
| | (Continued) | |

OTHER PUBLICATIONS

Communication Pursuant to Article 94(3) EPC Dated Sep. 4, 2023 From the European Patent Office Re. Application No. 19843063.9. (4 Pages).

(Continued)

*Primary Examiner* — Rochelle D Turchen
(74) *Attorney, Agent, or Firm* — Finnegan, Henderson, Farabow, Garrett & Dunner LLP

(57) ABSTRACT

A method for generating directional skin tightening, including:
  providing at least one alignment indication of at least one energy-emitting transducer;
  aligning at least one energy-emitting transducer on a surface of a skin according to the at least one alignment indication;
  applying energy by the at least one aligned energy-emitting transducer;
  generating directional skin tightening, by forming elongated spaced-apart thermal damage lesions in deep tissue layers of the skin arranged according to the alignment of said at least one energy-emitting transducer.

17 Claims, 18 Drawing Sheets

(56) References Cited

U.S. PATENT DOCUMENTS

| 5,664,570 | A | 9/1997 | Bishop |
| 6,595,934 | B1 | 7/2003 | Hissong et al. |
| 7,582,050 | B2 | 9/2009 | Schlorff et al. |
| 7,828,734 | B2 | 11/2010 | Azhari et al. |
| 8,133,180 | B2 | 3/2012 | Slayton et al. |
| 8,183,745 | B2 | 5/2012 | Trolier-McKinstry et al. |
| 10,194,526 | B1 | 1/2019 | Simula et al. |
| 2001/0029393 | A1 | 10/2001 | Tierney et al. |
| 2004/0039312 | A1 | 2/2004 | Hillstead et al. |
| 2004/0044375 | A1 | 3/2004 | Diederich et al. |
| 2004/0236375 | A1 | 11/2004 | Redding, Jr. |
| 2005/0251235 | A1 | 11/2005 | Schlorff et al. |
| 2006/0089632 | A1 | 4/2006 | Barthe et al. |
| 2007/0055179 | A1 | 3/2007 | Deem et al. |
| 2008/0071255 | A1 | 3/2008 | Barthe et al. |
| 2008/0139974 | A1 | 6/2008 | Da Silva |
| 2008/0183110 | A1 | 7/2008 | Davenport et al. |
| 2008/0195000 | A1* | 8/2008 | Spooner ............ A61H 23/0245 |
|  |  |  | 601/2 |
| 2008/0262482 | A1 | 10/2008 | Hantash et al. |
| 2009/0182231 | A1 | 7/2009 | Barthe et al. |
| 2009/0312693 | A1 | 12/2009 | Thapliyal et al. |
| 2010/0049186 | A1 | 2/2010 | Ingle et al. |
| 2011/0034833 | A1 | 2/2011 | Chopra et al. |
| 2011/0270137 | A1 | 11/2011 | Goren et al. |
| 2011/0272179 | A1 | 11/2011 | Vasoya |
| 2012/0016239 | A1 | 1/2012 | Barthe et al. |
| 2012/0016273 | A1 | 1/2012 | Diederich |
| 2012/0095372 | A1 | 4/2012 | Sverdlik et al. |
| 2012/0136280 | A1 | 5/2012 | Rosenberg et al. |
| 2012/0226214 | A1 | 9/2012 | Gurtner et al. |
| 2013/0068382 | A1 | 3/2013 | Harhen et al. |
| 2013/0134834 | A1 | 5/2013 | Yoshikawa et al. |
| 2013/0204167 | A1 | 8/2013 | Sverdlik et al. |
| 2013/0208572 | A1 | 8/2013 | Klee et al. |
| 2013/0245728 | A1 | 9/2013 | Galen et al. |
| 2013/0303904 | A1 | 11/2013 | Barthe et al. |
| 2014/0005521 | A1 | 1/2014 | Koehler et al. |
| 2014/0184022 | A1 | 7/2014 | Kobayashi et al. |
| 2015/0079069 | A1 | 3/2015 | Rozkov |
| 2015/0165241 | A1 | 6/2015 | Burdette |
| 2015/0217141 | A1 | 8/2015 | Baerthe et al. |
| 2015/0283408 | A1 | 10/2015 | Barthe et al. |
| 2015/0319880 | A1 | 11/2015 | Strickland et al. |
| 2016/0016015 | A1 | 1/2016 | Slayton et al. |
| 2016/0036412 | A1 | 2/2016 | Suzuki et al. |
| 2017/0273730 | A1 | 9/2017 | Walke et al. |
| 2018/0161016 | A1 | 6/2018 | Choi et al. |
| 2019/0009111 | A1 | 1/2019 | Myhr et al. |
| 2019/0105520 | A1 | 4/2019 | Sverdlik et al. |
| 2019/0110357 | A1 | 4/2019 | Gavagnin et al. |
| 2019/0132983 | A1 | 5/2019 | Weis et al. |
| 2019/0143149 | A1 | 5/2019 | Sverdlik et al. |
| 2019/0224501 | A1 | 7/2019 | Burdette |
| 2019/0254157 | A1 | 8/2019 | Kotlar |
| 2020/0287126 | A1 | 9/2020 | Chang |
| 2021/0298812 | A1 | 9/2021 | Sverdlik et al. |
| 2022/0008112 | A1 | 1/2022 | Sverdlik et al. |
| 2022/0015227 | A1 | 1/2022 | Ogawa et al. |
| 2022/0176167 | A1 | 6/2022 | Sverdlik et al. |
| 2023/0345615 | A1 | 10/2023 | Sverdlik et al. |

FOREIGN PATENT DOCUMENTS

| CN | 101232852 | 7/2008 |
| CN | 102098982 | 6/2011 |
| CN | 102958565 | 3/2013 |
| CN | 103371850 | 10/2013 |
| CN | 103987334 | 8/2014 |
| CN | 109475754 | 3/2019 |
| EP | 2629736 | 2/2017 |
| JP | H7-47079 | 2/1995 |
| JP | 2014-526313 | 10/2014 |
| JP | 2018-038814 | 3/2018 |
| KR | 10-2016-0110894 | 9/2016 |
| KR | 10-2018-0107832 | 10/2018 |
| WO | WO 00/45445 | 8/2000 |
| WO | WO 2006/114736 | 11/2006 |
| WO | WO 2008/103922 | 8/2008 |
| WO | WO 2010/029556 | 3/2010 |
| WO | WO 2012/018385 | 2/2012 |
| WO | WO 2013/033066 | 3/2013 |
| WO | WO 2013/184798 | 12/2013 |
| WO | WO 2014/022777 | 2/2014 |
| WO | WO 2015/075471 | 5/2015 |
| WO | WO 2016/090175 | 6/2016 |
| WO | WO 2015/106118 | 7/2017 |
| WO | WO 2017/212489 | 12/2017 |
| WO | WO 2018/035012 | 2/2018 |
| WO | WO 2020/026253 | 2/2020 |
| WO | WO 2020/026254 | 2/2020 |
| WO | WO 2020/194312 | 10/2020 |
| WO | WO 2021/111450 | 6/2021 |
| WO | WO 2022/144895 | 7/2022 |
| WO | WO 2023/089625 | 5/2023 |

OTHER PUBLICATIONS

Communication Pursuant to Article 94(3) EPC Dated May 23, 2023 From the European Patent Office Re. Application No. 17731653.6 (7 Pages).

Examination Report Dated Jun. 3, 2021 From the Australian Government, IP Australia Re. Application No. 2017278615. (5 Pages).

Examination Report Dated Nov. 30, 2021 From the Australian Government, IP Australia Re. Application No. 2017278615. (5 Pages).

Examination Report Dated Mar. 31, 2022 From the Australian Government, IP Australia Re. Application No. 2017278615. (3 Pages).

Final Official Action Dated Oct. 15, 2021 from the US Patent and Trademark Office Re. U.S. Appl. No. 16/211,288. (17 pages).

International Preliminary Report on Patentability Dated Jun. 6, 2024 From the International Bureau of WIPO Re. Application No. PCT/IL2022/051243 (11 Pages).

International Preliminary Report on Patentability Dated Oct. 7, 2021 From the International Bureau of WIPO Re. Application No. PCT/IL2020/050368. (8 Pages).

International Preliminary Report on Patentability Dated Feb. 11, 2021 From the International Bureau of WIPO Re. Application No. PCT/IL2019/050877. (13 Pages).

International Preliminary Report on Patentability Dated Feb. 11, 2021 From the International Bureau of WIPO Re. Application No. PCT/IL2019/050878. (10 Pages).

International Preliminary Report on Patentability Dated Jul. 13, 2023 From the International Bureau of WIPO Re. Application No. PCT/IL2021/051558 (12 Pages).

International Preliminary Report on Patentability Dated Jun. 16, 2022 From the International Bureau of WIPO Re. Application No. PCT/IL2020/051252. (11 Pages).

International Preliminary Report on Patentability Dated Dec. 20, 2018 From the International Bureau of WIPO Re. Application No. PCT/IL2017/050638. (16 Pages).

International Search Report and the Written Opinion Dated Jan. 2, 2018 From the International Searching Authority Re. Application No. PCT/IL2017/050638. (26 Pages).

International Search Report and the Written Opinion Dated Jun. 2, 2020 From the International Searching Authority Re. Application No. PCT/IL2020/050368. (36 Pages).

International Search Report and the Written Opinion Dated Mar. 2, 2023 From the International Searching Authority Re. Application No. PCT/IL2022/051243 (12 Pages).

International Search Report and the Written Opinion Dated Mar. 14, 2021 From the International Searching Authority Re. Application No. PCT/IL2020/051252. (16 Pages).

International Search Report and the Written Opinion Dated Jan. 22, 2020 From the International Searching Authority Re. Application No. PCT/IL2019/050877. (25 Pages).

(56)                    References Cited

OTHER PUBLICATIONS

International Search Report and the Written Opinion Dated Nov. 26, 2019 From the International Searching Authority Re. Application No. PCT/IL2019/050878. (17 Pages).

International Search Report and the Written Opinion Dated Apr. 27, 2022 From the International Searching Authority Re. Application No. PCT/IL2021/051558. (17 Pages).

Invitation to Pay Additional Fees and Communication Relating to the Results of the Partial International Search Dated Feb. 8, 2021 From the International Searching Authority Re. Application No. PCT/IL2020/051252. (4 Pages).

Invitation to Pay Additional Fees Dated Nov. 13, 2019 From the International Searching Authority Re. Application No. PCT/IL2019/050877. (2 Pages).

Invitation to Pay Additional Fees, Communication Relating to the Results of the Partial International Search and the Provisional Opinion Dated Oct. 6, 2017 From the International Searching Authority Re. Application No. PCT/IL2017/050638. (19 Pages).

Notice of Allowance Dated Apr. 22, 2022 together with Interview Summary Dated Apr. 11, 2022 from US Patent and Trademark Office Re. U.S. Appl. No. 16/211,288. (11 pages).

Notice of Allowance together with Interview Summary Dated Sep. 26, 2023 From the US Patent and Trademark Office Re. U.S. Appl. No. 18/215,971. (21 Pages).

Notice of Reasons for Rejection Dated Nov. 21, 2023 From the Japan Patent Office Re. Application No. 2021-553811. (3 Pages).

Notification of Office Action and Search Report Dated Sep. 2, 2020 From the China National Intellectual Property Administration Re. Application No. 201780044046.5 and Its Translation Into English. (10 Pages).

Notification of Office Action and Search Report Dated Nov. 6, 2023 From the National Intellectual Property Administration of the People's Republic of China Re. Application No. 202080039155.X and Its Machine Translation Into English. (26 Pages).

Notification of Office Action and Search Report Dated Nov. 9, 2023 From the National Intellectual Property Administration of the People's Republic of China Re. Application No. 202110669417.7 and Its Machine Translation Into English. (9 Pages).

Notification of Office Action and Search Report Dated Sep. 26, 2019 From the State Intellectual Property Office of the People's Republic of China Re. Application No. 201780044046.5. (10 Pages).

Official Action Dated Feb. 17, 2021 From the US Patent and Trademark Office Re. U.S. Appl. No. 16/211,288. (37 Pages).

Requisition by the Examiner Dated May 15, 2023 From the Innovation, Science and Economic Development Canada, Canadian Intellectual Property Office Re. Application No. 3,026,107. (4 pages).

Restriction Official Action Dated Oct. 5, 2023 From the US Patent and Trademark Office Re. U.S. Appl. No. 17/265,229. (8 pages).

Restriction Official Action Dated Oct. 27, 2020 from the US Patent and Trademark Office Re. U.S. Appl. No. 16/211,288. (8 pages).

Supplementary European Search Report and the European Search Opinion Dated Apr. 12, 2022 From the European Patent Office Re. Application No. 19843063.9. (7 Pages).

Supplementary European Search Report and the European Search Opinion Dated Nov. 20, 2023 From the European Patent Office Re. Application No. 20895471.9. (10 Pages).

Supplementary European Search Report and the European Search Opinion Dated Nov. 24, 2022 From the European Patent Office Re. Application No. 20776371.5 (9 pages).

Supplementary European Search Report and the European Search Opinion Dated Mar. 31, 2022 From the European Patent Office Re. Application No. 19844582.7. (9 Pages).

Third Party Observation Dated Aug. 11, 2023 Against Korea Republic Application No. 10-2021-7035100 and its Machine translation into English. (311 Pages).

Third Party Observation Dated Aug. 11, 2023 From the Korean Intellectual Property Office Re. Application No. 10-2021-7035100. (2 Pages).

Translation Dated Oct. 20, 2019 of Notification of Office Action Dated Sep. 26, 2019 From the State Intellectual Property Office of the People's Republic of China Re. Application No. 201780044046.5. (8 Pages).

Translation Dated Sep. 21, 2020 of Notification of Office Action Dated Sep. 2, 2020 From the China National Intellectual Property Administration Re. Application No. 201780044046.5. (8 Pages).

DiBernardo "Evaluation of Skin Tightening After Laser-Assisted Liposuction", Aesthet Surg Journal 29(5):400-407, Sep./Oct. 2009.

Epoxy Technology et al. "EPO-TEK Adhesives Applications", Epoxy Technology Inc., XP055410092, Data Sheets, p. 1-16, Dec. 31, 2013. p. 3-5.

Lee at al. "Flexible Piezoelectric Micromachined Ultrasonic Transducer (pMUT) for Application in Brain Stimulation", Microsystem Technologies, 23: 2321-2328, Published: Apr. 29, 2016.

Lin et al. "Prediction of Heat-Induced Collagen Shrinkage by Use of Second Harmonic Generation Microscopy", Journal of Biomedical Optics 11)3):034020-1-6, May 1, 2006.

Lumenis® "FemTouch™ Presentation", Lumenis®—Energy to Healthcare, CD-2003696 Rev. F, 40 P., 2018.

Massachusetts Institute of Technoloy "PDMS-MIT", 6.777J/2.751J Material Property Database, Massachusetts Institute of Technology, 2020.

Paul et al. "Three-Dimensional Radiofrequency Tissue Tightening: A Proposed Mechanism and Applications for Body", Aesthetic Plastic Surgery, 35(1):87-95, Sep. 11, 2010.

Tadir "International Update on Genitourinary Devices", ASLMS 2018, 38th Annual Conference of the American Society for Laser Medicine and Surgery, Dallas, TX, USA, Apr. 11-15, 2018, Poster Presentation, 20 P., Apr. 11, 2018.

Tadir et al. "Light and Energy Based Therapeutics for Genitourinary Syndrome of Menopause: Consensus and Controversies", Lasers in Surgery and Medicine, 49(2): 137-159, Published Online Feb. 21, 2017.

Wei et al. "Short-Term Effects of Radiofrequency Shrinkage Treatment for Anterior Cruciate Ligament Relaxation on Proprioception", Journal of International Medical Research, 41(5):1586-1593, Aug. 23, 2013.

Yasui et al. "Observation of Dermal Collagen Fiber in Wrinkled Skin Using Polarization-Resolved-Second-Harmonic-Generation Microscopy", Optics Express, 17(2): 912-923, Jan. 19, 2009.

Supplementary European Search Report and the European Search Opinion Dated Jul. 26, 2025 From the European Patent Office Re. Application No. 22895116.6. (13 Pages).

* cited by examiner

102

Fig. 5B
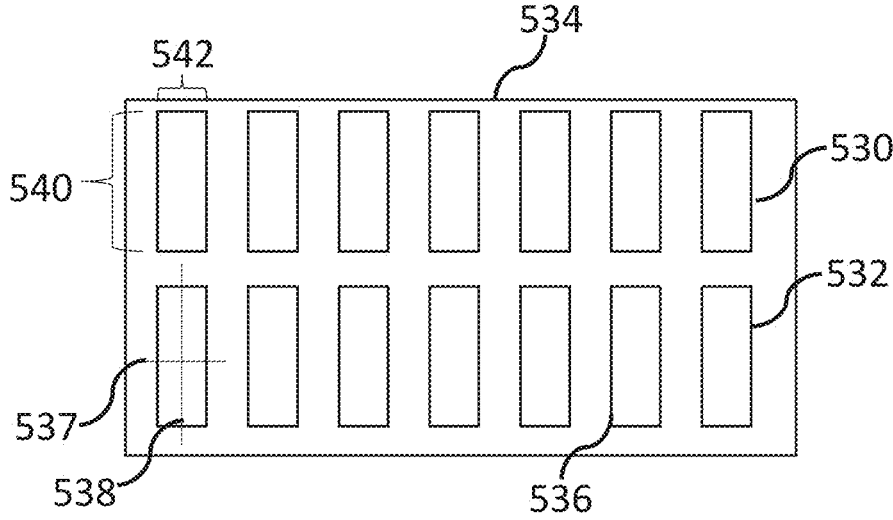
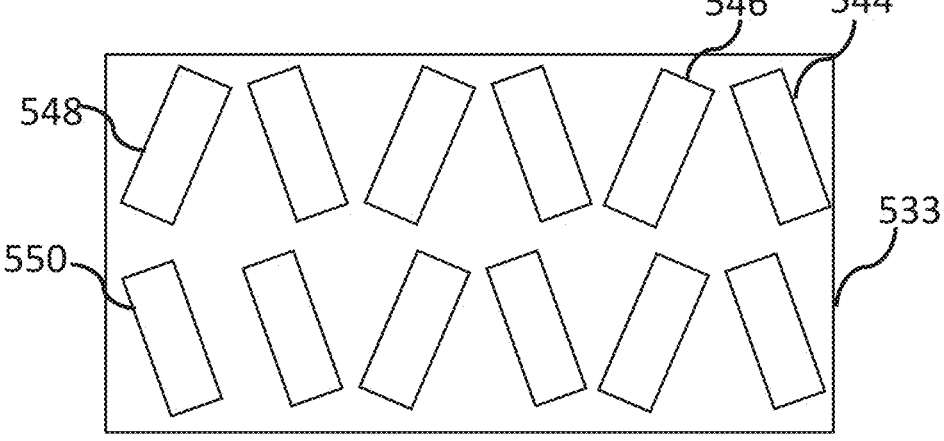
Fig. 5C

Fig. 12
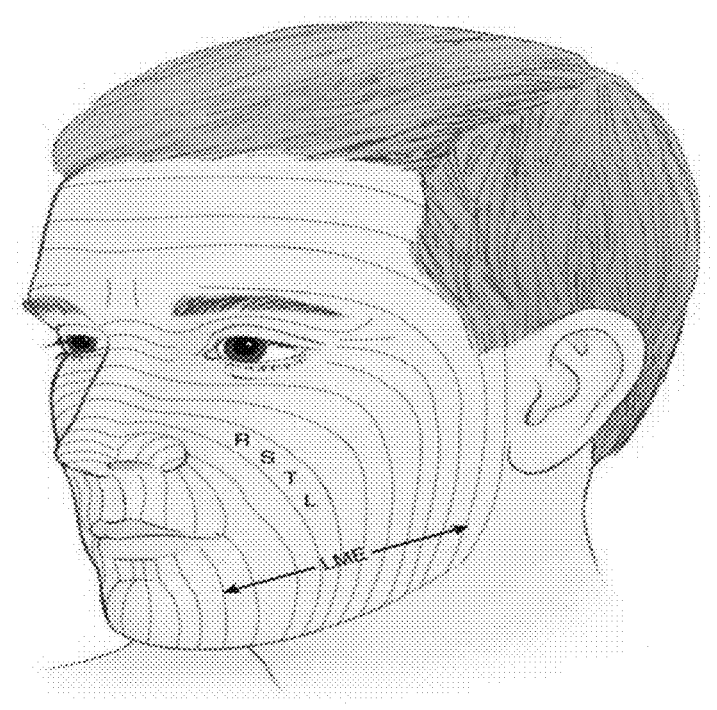
Fig. 13 (prior-art)
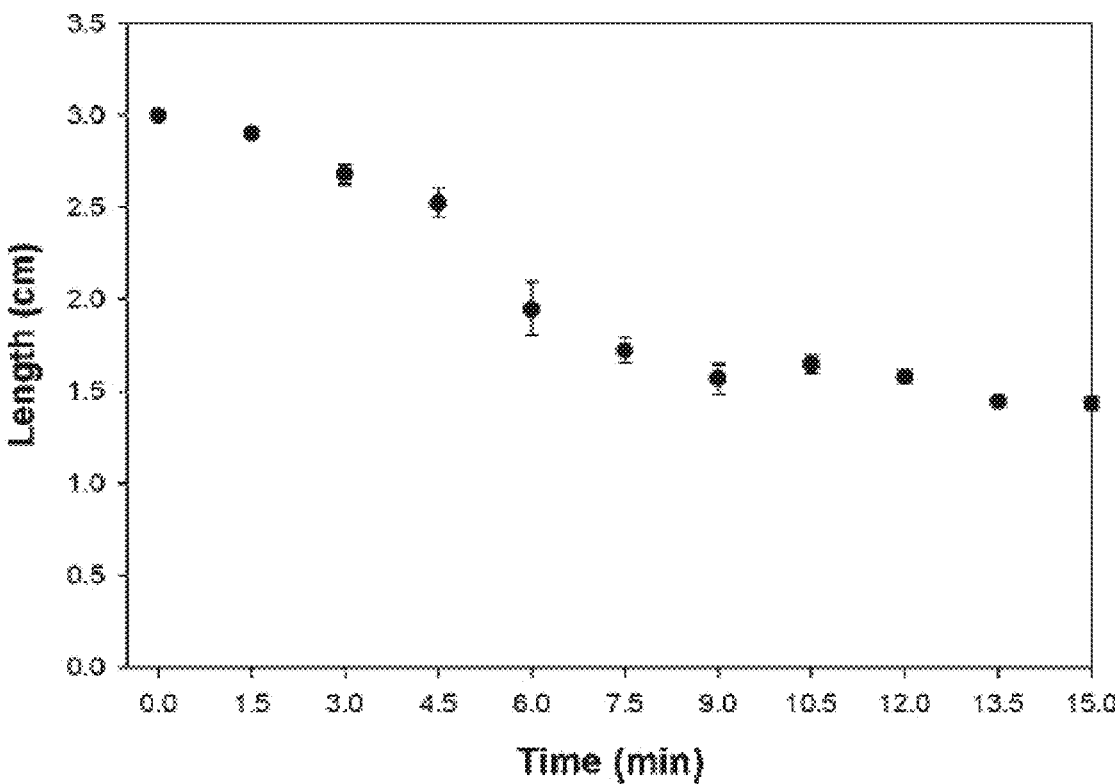

FIG. 16

VECTOR TIGHTENING

RELATED APPLICATIONS

This application is a National Phase of PCT Patent Application No. PCT/IL2022/051243 having International filing date of Nov. 22, 2022, which claims the benefit of priority under 35 USC § 119 (e) of U.S. Provisional Patent Application No. 63/281,802 filed on Nov. 22, 2021. The contents of the above applications are all incorporated by reference as if fully set forth herein in their entirety.

FIELD AND BACKGROUND OF THE INVENTION

The present invention, in some embodiments thereof, relates to skin tightening and, more particularly, but not exclusively, to directional skin tightening.

Facelift surgeries have evolved over the years from procedures aimed at superficially pulling the skin only, to procedures targeting deeper tissue volumes for more permanent and natural results. The early facelift procedures were developed about a hundred years ago and are commonly called "skin-only lift", which are involving only the skin and no other underlying tissue layer. A variation of this procedure called "mini-lift" is still being used in our modern era. The procedure generally consists of creating an incision close to the ear, undermining the skin of the lower face from the underlying muscles in the lower lateral face, pulling the undermined skin in a direction generally perpendicular to the RSTL lines, removing excess skin, and finally suture the skin edges together.

SUMMARY OF THE INVENTION

The following describes some examples of embodiments of the invention, some example of the invention are described herein and an embodiment may include features from more than one example and/or fewer than all features of an example:

Example 1. A method for generating directional skin tightening, comprising:

providing at least one alignment indication of at least one energy-emitting transducer;

aligning at least one energy-emitting transducer on a surface of a skin according to said at least one alignment indication;

applying energy by said at least one aligned energy-emitting transducer;

generating directional skin tightening, by forming elongated spaced-apart thermal damage lesions in deep tissue layers of the skin arranged according to the alignment of said at least one energy-emitting transducer.

Example 2. A method according to example 1, comprising determining at least one desired skin tightening vector of said skin; and generating said at least one alignment indication according to said determined at least one skin tightening vector.

Example 3. A method according to example 2, wherein said aligning comprises aligning said at least one energy-emitting transducer on said skin surface on said determined at least one desired skin tightening vector using said at least one alignment indication, and wherein said method comprises repeating said applying in at least two locations on said skin surface positioned along said at least one determined skin tightening vector.

Example 4. A method according to example 3, wherein said applying comprises moving a skin contacting surface of an ultrasound applicator comprising said at least one energy-emitting transducer between said two locations on said skin surface.

Example 5. A method according to any one of examples 3 or 4, wherein said elongated spaced-apart thermal damage lesions are axially arranged along said at least one determined skin tightening vector.

Example 6. A method according to any one of examples 2 to 5, wherein said determining comprises determining said at least one desired skin tightening vector based on position and/or orientation of at least one skin tension line on said skin surface.

Example 7. A method according to example 6, wherein said determined at least one desired skin tightening vector is oriented at an angle between 45° degrees and 135° degrees relative to said at least one skin tension line in said skin surface.

Example 8. A method according to example 7, wherein said at least one skin tension line comprise at least one of, Langer's lines, Cox's lines, Kraissel's lines, Rubin's lines, Straith's lines, Bulacio's lines, and relaxed skin tension lines (RSTL).

Example 9. A method according to any one of examples 2 to 8, wherein said determining comprises determining said at least one desired skin tightening vector based on position and/or orientation of at least one wrinkle on said skin surface.

Example 10. A method according to example 9, wherein said determined at least one desired skin tightening vector is oriented at an angle between 45° degrees and 135° degrees relative to said at least one wrinkle.

Example 11. A method according to any one of examples 2 to 10, wherein a minimal distance between two adjacent elongated spaced-apart thermal damage lesions along the determined at least one skin tension vector, is in a range of 0.1 mm to 20 mm.

Example 12. A method according to any one of examples 2 to 11, comprising controlling a depth of said applying according to depth and/or position of nerve tissue along the determined at least one skin tightening vector.

Example 13. A method according to any one of the previous examples, wherein said applying said energy comprises heating at least one tissue volume in said deep tissue layers of the skin to a temperature in a range of 50° C. to 80° C., to form at least one thermal damage lesion of said elongated spaced-apart thermal damage lesions.

Example 14. A method according to example 13, wherein said at least one tissue volume comprises collagen fibers, wherein said applying comprises applying said energy with parameter values sufficient to generate a partial denaturation of said collagen fibers in said at least one tissue volume.

Example 15. A method according to example 14, wherein said applying comprises applying said energy using at least one energy-emitting transducer having a long axis and a short axis, and wherein said applied energy generates contraction of collagen within said at least one tissue volume along the long axis of the at least one energy-emitting transducer.

Example 16. A method according to example 15, wherein a ratio between collagen contraction along the long axis of the at least one energy-emitting transducer and collagen contraction along the short axis of the at least one energy-emitting transducer is at least 1.5.

Example 17. A method according to any one of examples 14 to 16, wherein said applying comprises applying unfocused ultrasound energy to said deep tissue layers.

Example 18. A method according to example 17, wherein said unfocused ultrasound energy is applied with values of unfocused ultrasound energy parameters sufficient to at least partly denature said collagen fibers in the at least one thermal damage lesion, wherein said unfocused ultrasound energy parameters comprise at least one of, frequency of ultrasound waves, intensity of ultrasound waves, energy level per pulse of ultrasound energy delivered to the skin, and pulse duration.

Example 19. A method according to example 18, wherein a frequency of said ultrasound waves is in a range between 5 MHz-22 MHz.

Example 20. A method according to any one of examples 18 or 19, wherein an intensity of said ultrasound waves is in a range between 8-40 W/cm^2.

Example 21. A method according to any one of examples 18 to 20, wherein an energy level per pulse of ultrasound waves is in a range of 2-5 Joules.

Example 22. A method according to any one of examples 18 to 21, wherein a duration of each pulse of ultrasound energy is in a range of 1-10 seconds.

Example 23. A method according to any one of examples 2 to 16, wherein said applying comprises applying focused ultrasound energy or radiofrequency (RF) radiation to said deep tissue layers of the skin.

Example 24. A method according to any one of the previous examples, wherein said aligning comprises aligning said at least one energy emitting transducer on a skin surface of a face or neck of a subject.

Example 25. A method according to any one of the previous examples, wherein said generating comprises generating said directional skin tightening without cutting the skin of said subject.

Example 26. A method for according to any one of the previous examples, comprising: forming a facelift or a mini-facelift in said subject, by said applied energy forming said elongated spaced-apart thermal damage lesions.

Example 27. A method according to example 26, wherein said forming comprises forming said facelift or said mini-facelift without cutting the skin of a subject.

Example 28. A method according to any one of the previous examples, comprising:

cooling a surface of the skin during said applying to a temperature lower than 20° C.

Example 29. A method for generating directional skin tightening, comprising:

placing at least one elongated energy-emitting transducer in contact with a skin surface at a target treatment region, wherein said at least one elongated energy emitting transducer comprises a major axis and a minor axis;

applying energy by said at least one energy-emitting transducer into deep tissue layers of said skin comprising collagen;

generating shrinkage of said collagen by said applied energy, wherein a ratio between collagen shrinkage along said major axis, and collagen shrinkage along said minor axis of said at least one energy-emitting transducer is at least 1.5.

Example 30. A method according to example 29, whereon said deep tissue layers are located at a depth in a range between 0.5 mm to 5 mm from said skin surface.

Example 31. A method according to any one of examples 29 or 30, wherein said applying comprises heating at least one tissue volume in said deep tissue layers comprising said collagen to a temperature between 50-80° C. by said applied energy.

Example 32. A method according to any one of examples 29 to 31, wherein said applying comprises applying focused ultrasound energy or radiofrequency (RF) radiation to said deep tissue layers of the skin.

Example 33. A method according to any one of examples 29 to 31, wherein said applying comprises applying unfocused ultrasound energy to said deep tissue layers of the skin by delivering unfocused ultrasound waves through said skin surface.

Example 34. A method according to example 33, wherein a frequency of said delivered unfocused ultrasound waves is in a range between 5 MHz-22 MHz.

Example 35. A method according to any one of examples 33 or 34, wherein an intensity of said delivered unfocused ultrasound waves is in a range between 8-40 W/cm^2.

Example 36. A method according to any one of examples 33 to 35, wherein an energy level per pulse of said delivered unfocused ultrasound waves is in a range of 2-5 Joules.

Example 37. A method according to any one of examples 33 to 36, wherein a duration of each pulse of said delivered unfocused ultrasound waves is in a range of 1-10 seconds.

Example 38. A method according to any one of examples 29 to 37, comprising:

cooling said skin surface contacting said at least one elongated energy emitting transducer during said applying to a temperature lower than 25° C.

Example 39. A skin tightening system, comprising:

an applicator comprising at least one energy-emitting transducer configured to generate and deliver energy to skin tissue;

a user interface configured to deliver a human detectable indication to a user of the system;

a control circuitry functionally connected to said user interface;

wherein said control circuitry is configured to deliver at least one alignment indication of said at least one energy-emitting transducer by said user interface, and to signal said at least one energy-emitting transducer to generate and deliver said energy with parameter values sufficient to generate directional skin tightening in at least one skin region.

Example 40. A system according to example 39, wherein said user interface comprises a display, and wherein said control circuitry signals the user interface to deliver said at least one alignment indication on said display.

Example 41. A system according to any one of examples 39 or 40, comprising a memory, wherein said memory stores an indication of at least one desired skin tightening vector in said at least one skin region, and wherein said at least one alignment indication comprises information regarding said indication of said at least one desired skin tightening vector.

Example 42. A system according to example 41, wherein said indication of said at least one desired skin tightening vector stored in said memory comprises positioning information of two or more treatment locations along said at least one desired skin tightening vector, for placing said applicator and for delivery of said energy.

Example 43. A system according to example 42, wherein said control circuitry signals said user interface to generate a human detectable indication with information regarding a position and/or orientation of said applicator relative to a treatment location of said at least two treatment locations.

Example 44. A system according to example 43, wherein said applicator comprises at least one position and/or orientation sensor, and wherein said user interface generates said human detectable indication based on signals received from said at least one sensor.

Example 45. A system according to any one of examples 39 to 44, wherein said energy emitting transducer comprises at least one ultrasound transducer configured to deliver unfocused ultrasound energy to the skin, and wherein said control circuitry activates said ultrasound transducer according to values of activation parameters sufficient to at least partly denature collagen fibers in at least one tissue volume in deep tissue layers of the skin, wherein said activation parameters comprise at least one of, frequency of ultrasound waves, intensity of ultrasound waves, energy level per pulse of ultrasound energy delivered to the skin, and pulse duration.

Example 46. A system according to example 45, wherein said activation parameter values are sufficient to generate contraction of said collagen fibers along a long axis of said collagen fibers which is at least two times larger than a contraction generated by the activation parameter values of a short axis of said collagen fibers.

Example 47. A system according to any one of examples 45 or 46, wherein a frequency of said ultrasound waves is in a range between 5 MHz-22 MHz.

Example 48. A system according to any one of examples 45 to 47, wherein an intensity of said ultrasound waves is in a range between 8-40 W/cm^2.

Example 49. A system according to any one of examples 45 to 48, wherein an energy level per pulse of ultrasound waves is in a range of 2-5 Joules.

Example 50. A system according to any one of examples 45 to 49 wherein a duration of each pulse of ultrasound energy is in a range of 1-10 seconds.

Example 51. A system according to any one of examples 45 to 50, comprising a cooling module, configured to cool said at least one ultrasound transducer to a temperature lower than 25° C., during the activation of said at least one ultrasound transducer by said control circuitry.

Example 52. A system according to example 39 for use in a method for generating cosmetic non-therapeutic directional skin tightening, wherein said method comprises:

providing at least one alignment indication of said at least one energy-emitting transducer;

aligning said at least one energy-emitting transducer on a surface of a skin according to said at least one alignment indication;

applying energy by said at least one aligned energy-emitting transducer;

repeating said aligning and said applying until a cosmetically beneficial directional skin tightening is generated.

Example 53. A method for generating cosmetic non-therapeutic directional skin tightening, comprising:

providing at least one alignment indication of at least one energy-emitting transducer;

aligning at least one energy-emitting transducer on a surface of a skin according to said at least one alignment indication;

applying energy by said at least one aligned energy-emitting transducer;

repeating said aligning and said applying until a cosmetically beneficial directional skin tightening is generated.

Example 54. A method according to example 53, comprising determining at least one desired skin tightening vector of said skin; and generating said at least one alignment indication according to said determined at least one skin tightening vector.

Example 55. A method according to example 54, wherein said repeating comprises repeating said aligning and said applying until a cosmetically beneficial directional skin tightening is generated in said at least one desired skin tightening vector;

Example 56. A method according to any one of examples 54 or 55, wherein said aligning comprises aligning said at least one energy-emitting transducer on said skin surface on said determined at least one desired skin tightening vector using said at least one alignment indication, and wherein said repeating comprises repeating said applying in at least two locations on said skin surface positioned along said at least one determined skin tightening vector.

Example 57. A method according to example 56, wherein said applying comprises moving a skin contacting surface of an ultrasound applicator comprising said at least one energy-emitting transducer between said two locations on said skin surface.

Example 58. A method according to any one of examples 56 or 57, comprising:

forming elongated spaced-apart thermal damage lesions in deep tissue layers of the skin arranged according to the alignment of said at least one energy-emitting transducer, and wherein said cosmetically beneficial directional skin tightening is generated by said forming.

Example 59. A method according to example 58, wherein said elongated spaced-apart thermal damage lesions are axially arranged along said at least one determined skin tightening vector.

Example 60. A method according to any one of examples 54 to 59, wherein said determining comprises determining said at least one desired skin tightening vector based on position and/or orientation of at least one skin tension line on said skin surface.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, some embodiments of the present invention may be embodied as a system, method or computer program product. Accordingly, some embodiments of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present invention may take the form of a computer program product embodied in one or more computer readable medium(s) having computer readable program code embodied thereon. Implementation of the method and/or system of some embodiments of the invention can involve performing and/or completing selected tasks manually, automatically, or a combination thereof. Moreover, according to actual instrumentation and equipment of some embodiments of the method and/or system of the invention, several selected tasks could be implemented by hardware, by software or by firmware and/or by a combination thereof, e.g., using an operating system.

For example, hardware for performing selected tasks according to some embodiments of the invention could be implemented as a chip or a circuit. As software, selected tasks according to some embodiments of the invention could be implemented as a plurality of software instructions being executed by a computer using any suitable operating system. In an exemplary embodiment of the invention, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments of the invention. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present invention may be described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Some of the methods described herein are generally designed only for use by a computer, and may not be feasible or practical for performing purely manually, by a human expert. A human expert who wanted to manually perform similar tasks, such as plan a tension vector, identify location of skin tension lines, identify treatment regions along a planned tension vector, identify a position of an applicator relative to a planned tension vector and/or at least one treatment region, might be expected to use completely different methods, e.g., making use of expert knowledge and/or the pattern recognition capabilities of the human brain, which would be vastly more efficient than manually going through the steps of the methods described herein.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 5B and 5C are schematic illustrations showing different arrangements of ultrasound transducers on an applicator;

FIG. 12 is a schematic illustration showing lines of maximal extensibility (LME) and Relaxed Skin Tension Lines (RSTL);

FIG. 13 is a graph showing Changes of length of rat tail tendon from thermal treatment at 58° C., error bars represent calculated standard deviations;

FIG. 16 shows in the left panel—the collagen deformation field $\xi$ is integrated in one direction and plotted in a perpendicular plane. In this example, $\xi$ is integrated along the red arrows in the y direction and plotted on the hatched plane in yellow (the xz plane), and in the right panel—the projection results are shown in 3 perpendicular planes.

DESCRIPTION OF SPECIFIC EMBODIMENTS OF THE INVENTION

Figure 1A:
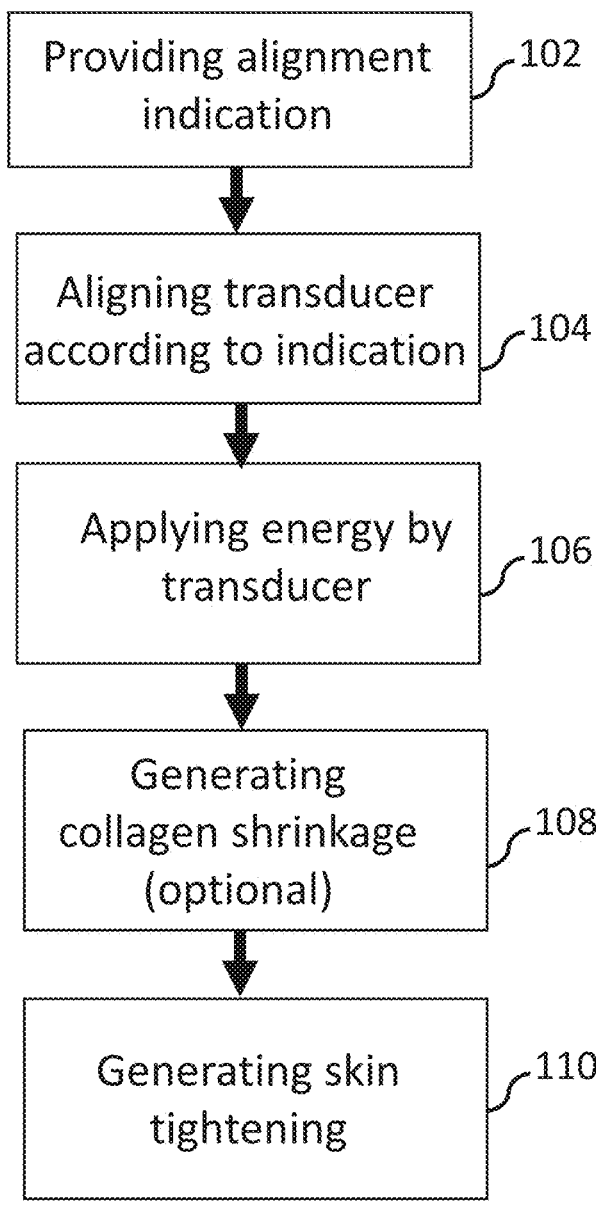
FIG. 1A is a flow chart of a process for generating skin tightening, according to some exemplary embodiments of the invention.

The present invention, in some embodiments thereof, relates to skin tightening and, more particularly, but not exclusively, to directional skin tightening.

An aspect of some embodiments relates to forming at least one desired tension vector in a skin, along a specific selected direction. In some embodiments, the tension vectors are formed by generating fractionated thermal damage lesions in the selected direction. In some embodiments, the tension vectors direction is a direction selected for generating a non-surgical facelift or a non-surgical mini-facelift in the subject, for example without cutting the subject skin.

According to some embodiments, the selected direction is selected according to a position and/or orientation of wrinkles on the skin. Alternatively or additionally, the selected direction is selected according to position and/or orientation of skin tension lines, for example relaxed skin tension lines (RSTL). Alternatively or additionally, the selected direction is selected according to a position and/or orientation of collagen fibers in the skin.

According to some exemplary embodiments, a skin tightening effect, which is optionally similar to an effect of a facelift or a mini-facelift, is generated by forming thermal damage lesions in deep tissue layers of the skin along the tension vectors. As used herein, the term along a tension vector means that at least 50% of the thermal damage lesions are formed in a direction which is substantially parallel the tension vector and/or in the location of the tension vector.

According to some embodiments, the tension vectors are formed by orientating at least one energy-emitting transducer, for example a radio frequency (RF) transducer or an ultrasound transducer, along the selected direction. Optionally, the at least one energy-emitting transducer comprises an unfocused ultrasound transducer. In some embodiments, the at least one transducer comprises an elongated transducer or a transducer that has an elongated energy-emitting surface. In some embodiments, the tension vectors are formed by orientating, for example aligning, a long axis of the transducer with the selected direction. Alternatively or additionally, the at least one energy-emitting transducer, for example an elongated transducer or a non-elongated transducer, is moved along the selected direction.

According to some embodiments, the tension vectors are formed as straight lines. Alternatively, the tension vectors are formed as jagged lines or as curved lines. In some embodiments, a length and/or shape of the formed lines is based on at least one of, the type of skin tension lines, a distance between two adjacent lines, density of wrinkles at the target location, depth of wrinkles at the target location, skin tissue composition at the target location, and a presence and/or location of scar tissue at the target location.

According to some embodiments, at least one tension vector is formed in a selected global skin tightening direction which is similar to a global skin tightening direction selected for a facelift or a mini facelift procedure. Alternatively or additionally, the at least one tension vector is formed relative to one or more existing skin tension lines. Alternatively, the at least one tension vector is formed locally, to generate a local skin tightening effect, for example to treat specific wrinkles of a subject.

Figure 1B:
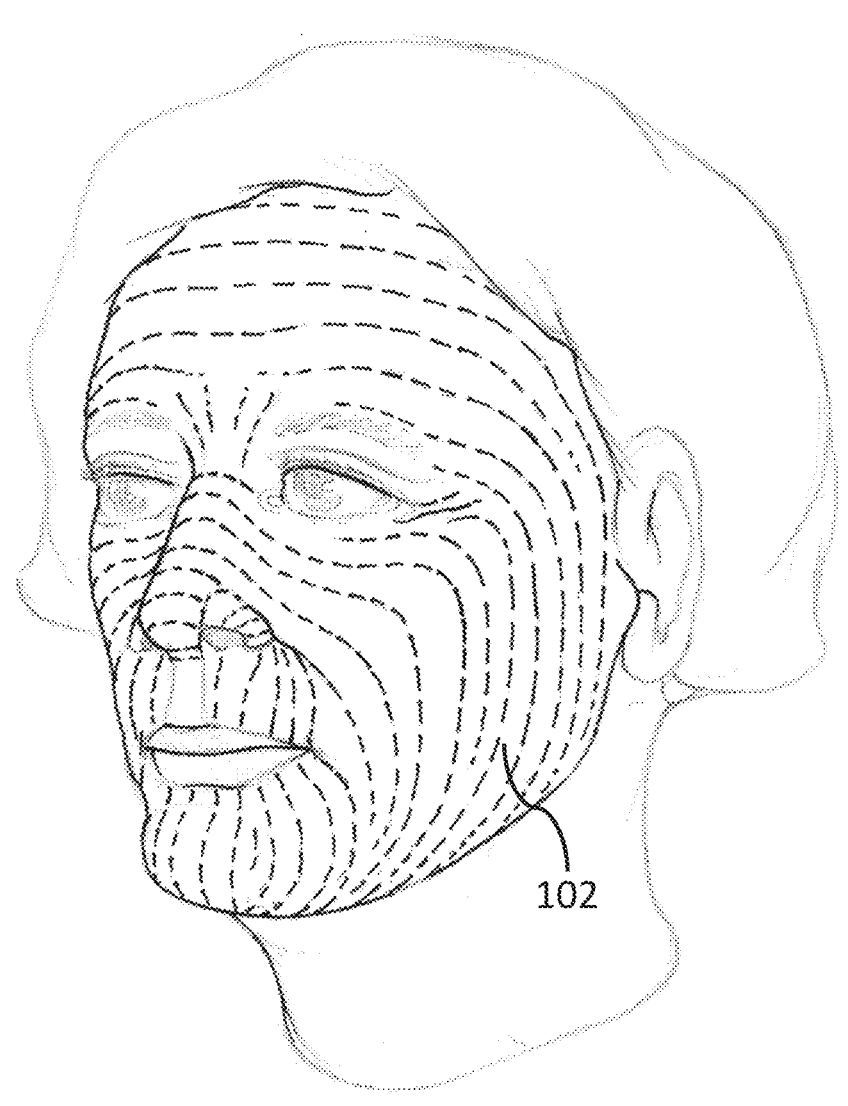
FIG. 1B is a schematic illustration of skin relaxation lines on a face and neck of a human subject, according to some exemplary embodiments of the invention.

According to some embodiments, skin tension lines comprise Langer's lines, Cox's lines, Kraissel's lines, Rubin's lines, Straith's lines, Bulacio's lines, and RSTL. In some embodiments, RSTL, also known as "Langer's Line" are shown in FIGS. 1A-B, for example line 102.

RSTL lines have the same directional shape from one person to another, but can vary slightly. Optionally, the RSTL lines run parallel to a molecular orientation of collagen and may therefore indicate collagen alignment. Optionally, the natural wrinkles of the skin follow the RSTL lines and may be used to locate their orientations.

According to some embodiments, energy, for example ultrasound energy, is applied to deep tissue layers of the skin by one or more energy emitting transducers, for example ultrasound transducers. In some embodiments, the energy is applied with parameter values which are sufficient to heat tissue volumes in said deep tissue layers to a temperature in a range between 50° C. to 90° C., for example in a range between 50° C. to 80° C., in a range between 55° C. to 75° C., in a range between 65° C. to 85° C. or any intermediate, smaller or larger range of values. In some embodiments, the energy is applied with parameter values which are sufficient to heat tissue volumes in said deep tissue layers to a temperature in a range between 65° C.-75° C., for a time period between 2 seconds and 5 seconds.

According to some embodiments, ultrasound energy, for example unfocused ultrasound energy is applied by at least one ultrasound transducer. In some embodiments, the ultrasound energy is applied by ultrasound waves having intensity values in a range between 8-40 W/cm^2, for example 8-15 W/cm^2, 10-20 W/cm^2, 12-30 W/cm^2 or any intermediate, smaller or larger range of values.

According to some embodiments, a frequency of the applied ultrasound waves is in a range between 5-22 MHz, for example 5-10 MHz, 5-15 MHz, 9-22 MHz, or any intermediate, smaller or larger range of values.

According to some embodiments, an energy level per pulse of the ultrasound energy is in a range between 2-5 Joules, for example 2-4 Joules, 3-5 Joules, or any intermediate, smaller or larger range of values.

According to some embodiments, a duration of each pulse of ultrasound energy is in a range of 1-10 seconds, for example in a range of 1-4 seconds, 2-6 seconds, 3-6 seconds, 4-10 seconds, or any intermediate, smaller or larger range of values.

According to some embodiments, the heated tissue volumes comprise collagen fibers, and the heating temperature and energy pulse duration (time) are sufficient to at least partly denature the collagen fibers. In some embodiments, in order to denature collagen a thermal dose delivered to the tissue is in a range between about 0.1 to about 10, according to the Arrhenius equation, for example a thermal dose in a range between 0.1-3, 0.1-5, 1-4, 2-6, 3-8, and 5-10, according to the Arrhenius equation. The thermal dose, calculated using the Arrhenius equation takes into consideration the tissue temperature and heating time. In some embodiments, in order to reach a thermal dose of 0.1-10, an energy level of the delivered ultrasound energy is in a range between 3-5 Joules, as described previously.

An aspect of some embodiments relates to generating directional skin tightening by generating directional collagen shrinkage. In some embodiments, the directional collagen shrinkage is formed by application of energy to deep tissue layers of skin which contain collagen. In some embodiments, the energy is applied with parameter values that are sufficient to heat the collagen to temperature levels that at least partly denatures the collagen.

According to some embodiments, the energy is applied by at least one elongated energy-emitting transducer. In some embodiments, the elongated energy-emitting transducer having at least one major axis and at least one minor axis. In some embodiments, collagen shrinkage generated by the at least one transducer is larger along the major axis of the transducer relative to collagen shrinkage along the minor axis of the transducer. In some embodiments, a ratio between collagen shrinkage along the major axis of the transducer and collagen shrinkage along the minor axis of the transducer is at least 1.1, for example at least 1.2, at least 1.4, at least 1.5, at least 2, or any intermediate, smaller or larger ratio.

According to some exemplary embodiments, the directional collagen shrinkage is aligned with a formation of a desired at least one tension vector of the skin. In some embodiments, the desired at least one tension vector is formed by forming fractionated regions of directional collagen shrinkage regions in deep tissue layers of the skin, along the desired skin tension vector. In some embodiments, the fractionated regions are formed by at least two spaced-apart energy-emitting transducers of an applicator. Alternatively or additionally, the fractionated regions are formed by moving at least one energy-emitting transducer along, for example an elongated energy-emitting transducer along the desired tension vector.

According to some embodiments, the energy is applied with parameter values which are sufficient to heat tissue volumes in said deep tissue layers containing the collagen to a temperature in a range between 50° C. to 90° C., for example in a range between 50° C. to 80° C., in a range between 55° C. to 75° C., in a range between 65° C. to 85° C. or any intermediate, smaller or larger range of values. In some embodiments, the energy is applied with parameter values which are sufficient to heat the tissue volumes in said deep tissue layers to a temperature in a range between 65° C.-75° C., for a time period between 2 seconds and 5 seconds.

Figures 4A, 4B, 4C:
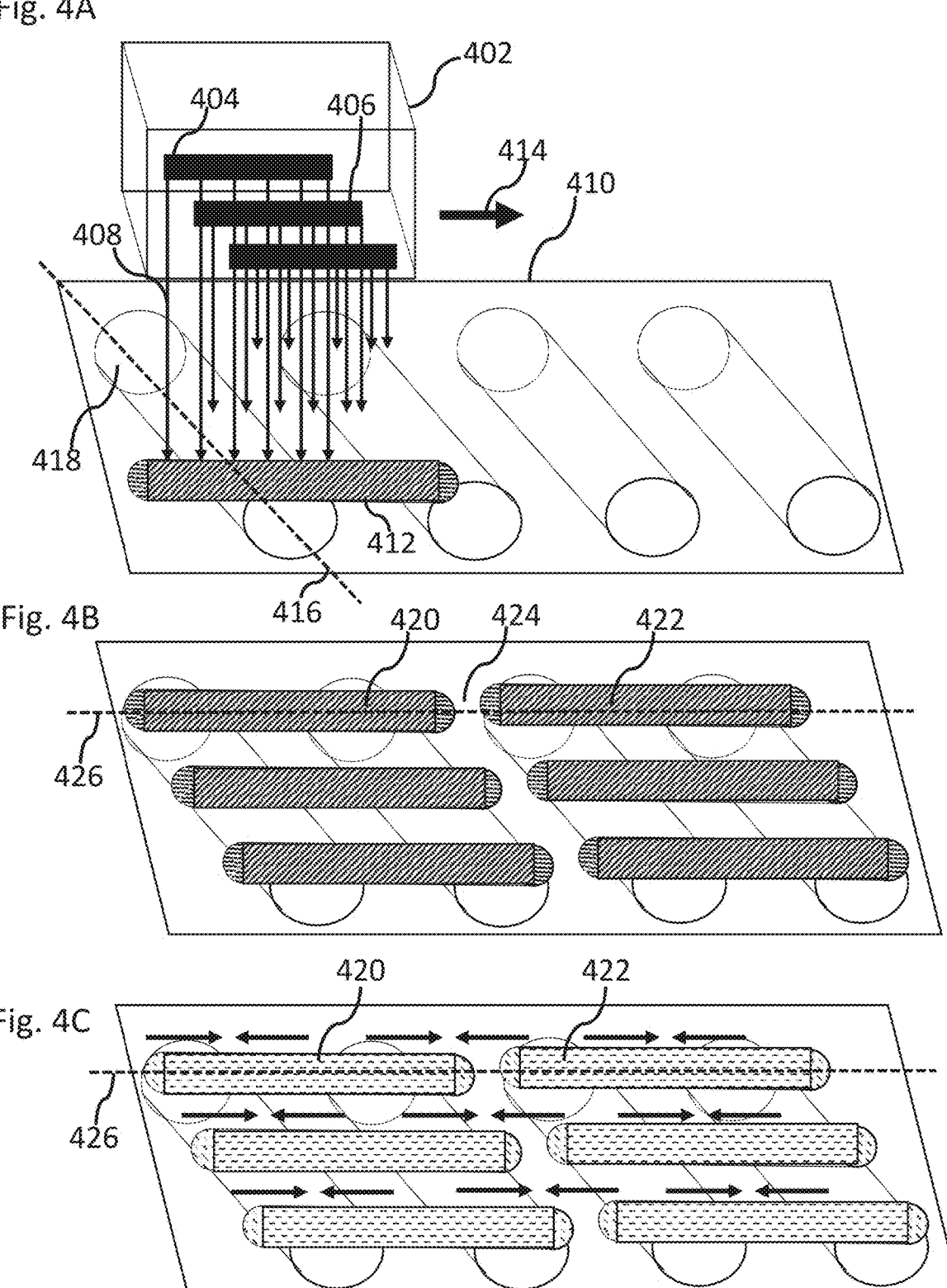
FIGS. 4A-4C are schematic illustrations showing skin tightening relative to collagen fibers alignment following a skin tightening treatment, according to some exemplary embodiments of the invention.
Figure 5A:
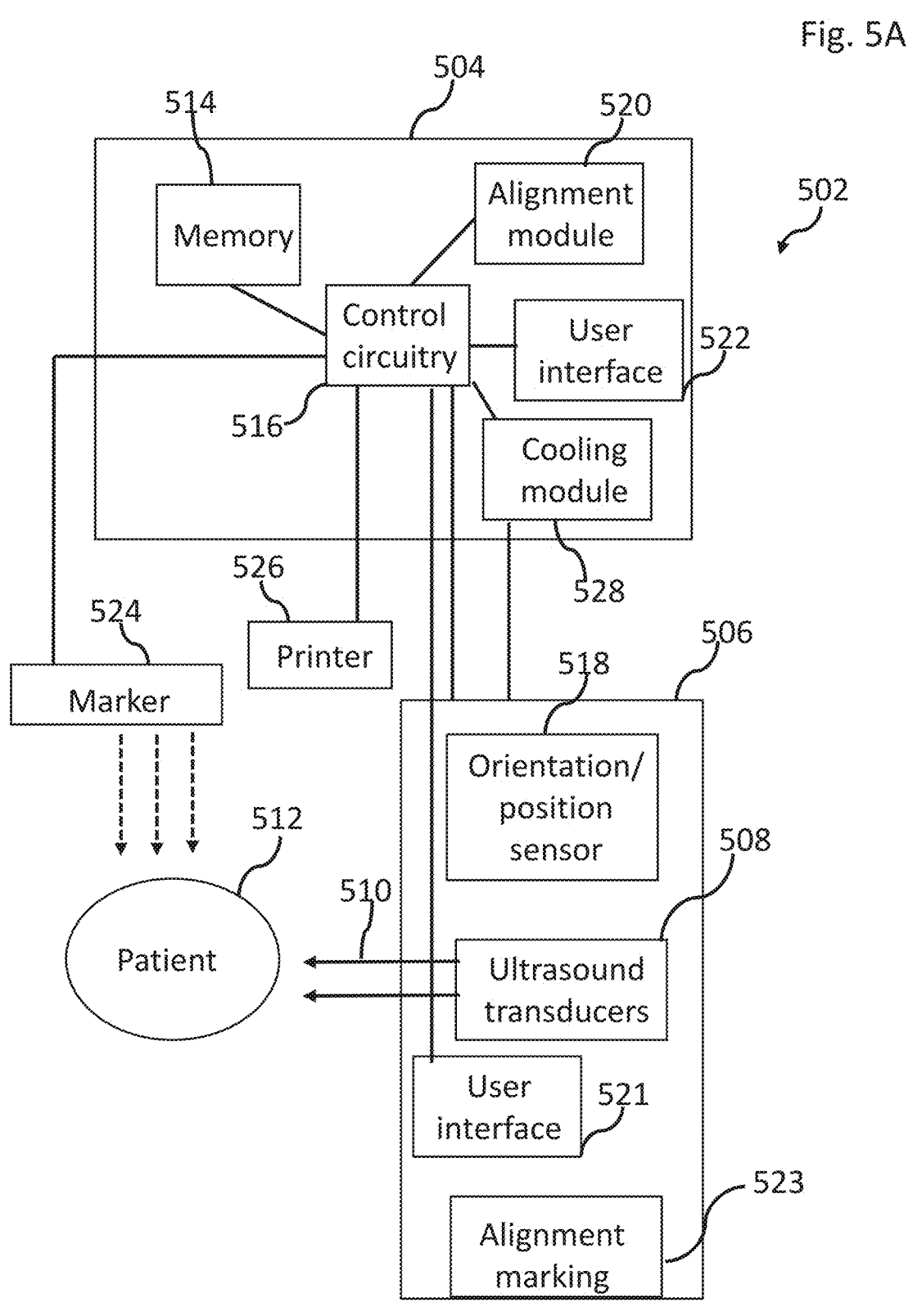
FIG. 5A is a block diagram of a system for delivery of a directional skin tightening, according to some exemplary embodiments of the invention.

According to some embodiments, one or more of the methods described herein, for example in FIGS. 1A, 2, 6A, 6B, are used in order to generate a cosmetically beneficial directional skin tightening, for example a directional skin tightening that is in a desired or a planned direction and has a desired or a planned skin tightening level and/or a directional skin tightening that allows to have a desired or a planned appearance of the skin. In some embodiments, one or more of the systems described herein, for example in FIGS. 4A and 5A, are used in a method for generating a cosmetically beneficial directional skin tightening. In some embodiments, the methods described herein are cosmetic non-therapeutic methods, having an effect restricted to a skin layer of the body, for example an effect restricted to skin layers between skin surface and the hypodermis, for example an effect restricted to the epidermis and/or to the dermis skin layers.

In some embodiments, the one or more transducers of the applicator contact the skin surface indirectly, for example via at least one of a film, coating, gel, or any layer placed between the one or more ultrasound transducers and the skin surface.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Process for Generating Skin Tightening

According to some exemplary embodiments, skin tightening is generated using at least one energy emitting transducer, for example an ultrasound transducer or a radiofrequency (RF) electrode. In some embodiments, the ultrasound transducer comprises an ultrasound transducer configured to generate unfocused, for example non-converging, ultrasound waves. In some embodiments, energy applied through a skin surface into deep tissue layers generates skin tightening is generated along at least one desired skin tightening vector. Additionally or optionally, the skin tightening is generated due to shrinkage of collagen in deep tissue layers of the skin, heated by the applied energy.

Reference is now made to FIG. 1A, depicting a process for generating directional skin tightening, according to some exemplary embodiments of the invention.

According to some exemplary embodiments, at least one alignment indication is provided at block 102. In some embodiments, the at least one alignment indication comprises an indication for an alignment of at least one energy-emitting transducer, for example an ultrasound transducer, on a skin surface. Alternatively or additionally, the at least one alignment indication comprises an indication for an alignment of an applicator comprising the energy-emitting transducer, for example the ultrasound transducer, on the skin surface. As non-limiting examples, in some embodiments, the alignment indication comprises at least one marking on an applicator, for example an elongated shape printed or molded on the applicator, an applicator part line, or an applicator side.

According to some exemplary embodiments, the at least one alignment indication is based on a desired skin tension vector. In some embodiments, the desired skin tension vector is determined according to at least one wrinkle on a skin and/or according to existing skin tension lines. In some embodiments, the skin tension lines comprise Langer's lines, Cox's lines, Kraissel's lines, Rubin's lines, Straith's lines, Bulacio's lines, and RSTL, for example lines 120 shown in FIG. 1B. Alternatively or additionally, the desired skin tension vector is determined according to a type and/or location of a cosmetic procedure, for example a facelift of a mini-facelift that is performed using at least one method and/or a system described in this application, without cutting the skin.

According to some exemplary embodiments, the at least one alignment indication comprises a human detectable indication, provided as a visual indication and/or as an audio indication.

According to some exemplary embodiments, the at least one energy-emitting transducer is placed in contact with the skin surface, and is aligned according to the alignment indication, at block 104. Alternatively or additionally, an applicator comprising the at least one energy-emitting transducer, is aligned on the skin surface according to the provided alignment indication.

According to some exemplary embodiments, energy is applied by the energy-emitting transducer at block 106. In some embodiments, the applied energy comprises unfocused ultrasound energy. In some embodiments, the energy is transcutaneously applied to at least one tissue volume located in deep tissue layers of the skin, for example at least one tissue volume located at a depth between 0.5 mm and 5 mm from the skin surface. In some embodiments, the at least one tissue volume comprises collagen, optionally arranged as elongated fibers.

According to some exemplary embodiments, the applied energy heats the at least one tissue volume to a temperature in a range between 50-80° C., for example 50-60° C., 55-70° C., 60-75° C., 60-80° C. or any intermediate, smaller or larger range of temperatures. In some embodiments, prior to, during and/or after the energy application the surface of the skin, for example the skin surface contacting the at least one energy-emitting transducer is cooled, optionally via the at least one energy-emitting transducer. In some embodiments, the skin surface is cooled to a temperature lower than 25° C., for example lower than 22° C., lower than 20° C. or any intermediate, smaller or larger temperature.

According to some exemplary embodiments, the applied energy generates thermal damage lesions, for example fractionated thermal damage lesions in deep tissue layers of the skin. Optionally, the thermal damage lesions are elongated lesions. In some embodiments, the thermal damage lesions are spaced-apart lesions. In some embodiments, the fractionated thermal damage lesions are located a depth in a range of 0.5-5 mm, for example 0.5-2 mm, 1-4 mm, 2-5 mm or any intermediate, smaller or larger range of values from an epidermis or from a surface of the skin. In some embodiments, the thermal damage lesions are arranged and/or oriented, for example relative to each other, according to the alignment of the at least one energy-emitting transducer, for example at least one ultrasound transducer.

In some embodiments, a distance between two adjacent thermal damage lesions is in a range between 0.1 mm to 5 mm, for example 0.1 mm to 0.5 mm, 0.2 mm to 1 mm, 0.5 mm to 2 mm, 1 mm to 3 mm, 2 mm to 5 mm, or any intermediate, smaller or larger range of values. In some embodiments, the fractionated thermal damage lesions comprises denatured collagen fibers. In some embodiments, the collagen fibers are denatured in the thermal damage lesions in a percentage range between 2% to 60%, for example 2% to 10%, 5% to 30%, 15% to 50%, 20% to 55% or any intermediate, smaller or larger range of values. According to some exemplary embodiments, the energy is applied at block 106 intermittently. In some embodiments, the energy is applied at two or more locations on the skin surface located on the desired at least one skin tension vector. In some embodiments, the at least one energy-emitting transducer is moved between the two or more locations during the energy application, for example when the energy application stops after energy application at a first location and before initiating energy application at a second location of the two or more locations.

According to some exemplary embodiments, the applied energy optionally shrinks the collagen in the at least one tissue volume, at block 108. In some embodiments, the applied energy at least partly denatures the collagen within the at least one tissue volume. In some embodiments, the at least one energy-emitting transducer has at least one long axis and at least one short axis. In some embodiments, a ratio between collagen shrinkage along the at least one long axis of the transducer and collagen shrinkage along the at least one short axis of the transducer is at least 1.5, for example at least 2, at least 2.5, at least 3, or any intermediate, smaller or larger value.

According to some exemplary embodiments, skin tightening is generated at block 110. In some embodiments, the skin tightening is generated without cutting the skin. In some embodiments, the skin tightening is formed in facial and/or neck regions. In some embodiments, the skin tightening is generated by the collagen shrinkage in the deep tissue layers of the skin.

Exemplary Process for Forming Tension Vectors

Figure 2:
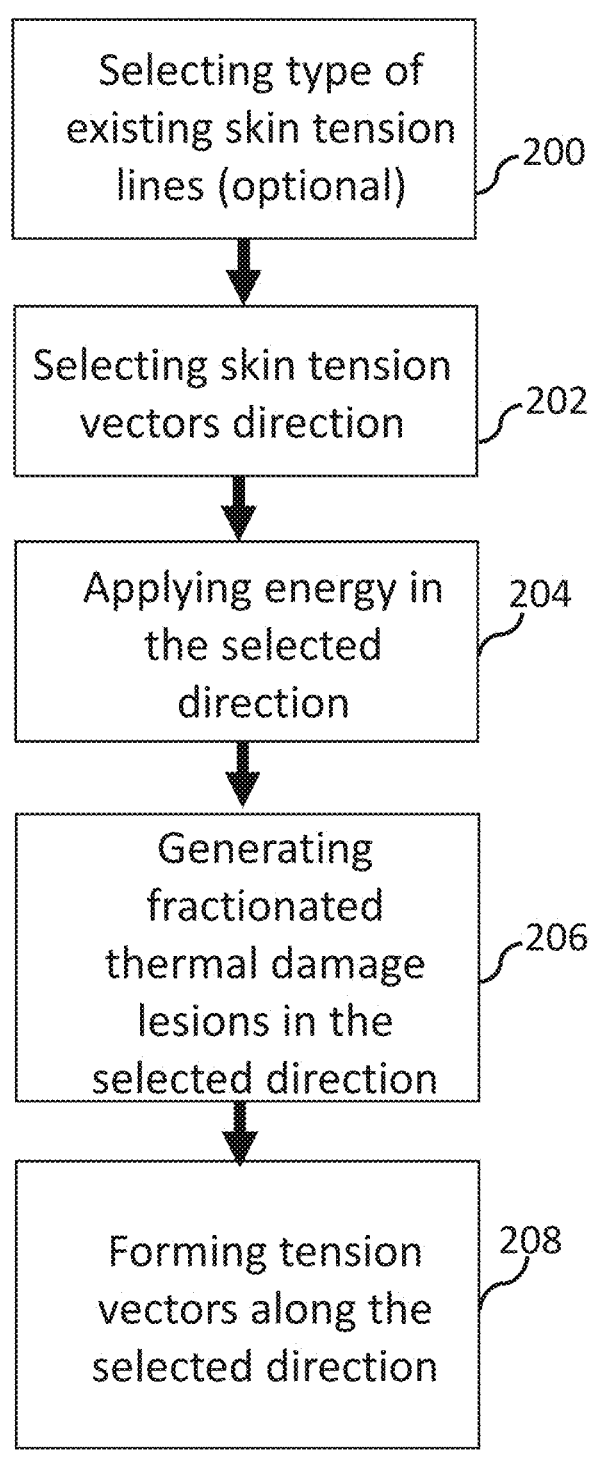
FIG. 2 is a flow chart of a process for forming tension vectors along a selected direction, according to some exemplary embodiments of the invention.

According to some exemplary embodiments, during a process for skin tightening, skin tension vectors are formed in the skin tissue. In some embodiments, the skin tension vectors are formed in a target region of facial skin, for example as part of a cosmetic procedure. In some embodiments, the cosmetic procedure is a facelift procedure comprising a full facelift, a partial facelift and a mini facelift. Alternatively or additionally, the cosmetic procedure comprises a procedure for minimizing an appearance of wrinkles and/or scars. In some embodiments, the skin tension vectors are generated along a selected direction in the skin. Reference is now made to FIG. 2, depicting processes for generating skin tension vectors, according to some exemplary embodiments of the invention.

According to some exemplary embodiments, a type of existing skin tension lines is optionally selected at block 200. In some embodiments, the type of existing skin tension lines comprise at least one of, Langer's lines, Cox's lines, Kraissel's lines, Rubin's lines, Straith's lines, Bulacio's lines, and RSTL. In some embodiments, the type of existing skin tensions lines is selected based on a location of a target skin region for a skin tightening treatment.

According to some exemplary embodiments, a desired direction, for example a target direction, of skin tension vectors is selected at block 202. In some embodiments, the desired direction is selected in a target skin region. In some embodiments, the desired direction is selected based on at least one of, location, orientation, and density of wrinkles in the target skin region and/or in the vicinity of the target skin region. Alternatively or additionally, the desired direction is selected according to existing skin tension lines, for example existing skin tension lines in the target skin region and/or in the vicinity of the target skin region.

Alternatively or additionally, the desired direction is selected according to at least one of, skin composition, location of nerve tissue, location of blood vessels, and/or location of scar tissue in the target skin region. Optionally, the direction of skin tension vectors is selected to avoid and not to pass through scar tissue.

According to some exemplary embodiments, selecting a direction at block 202 optionally comprises determining an orientation, for example an angle between the skin tension vectors and one or more wrinkles, and/or between the skin tension vectors and existing skin tension lines of a skin tension lines type selected at block 200.

According to some exemplary embodiments, selecting a direction at block 202 optionally comprises determining a shape and/or length of the skin tension vectors. In some embodiments, the shape and/or length of the skin tension vectors is determined based on the location and/or shape of wrinkles in the target skin region. Alternatively or additionally, the shape and/or length of the skin tension vectors is determined based on existing skin tissue lines. Alternatively or additionally, the shape and/or length of the skin tension vectors is determined based on skin tissue composition, for example based on a location of scar tissue in the target skin region.

According to some exemplary embodiments, energy is applied to the target skin region, at block 204. In some embodiments, the applied energy comprises RF energy and/or ultrasound energy. In some embodiments, the ultrasound energy comprises focused ultrasound energy and/or unfocused ultrasound energy. In some embodiments, the energy is applied to the skin tissue, for example as described in application WO2017/212489 filed on 6 Jun. 2017. Optionally, the energy is applied to the tissue while cooling the external surface of the skin.

According to some exemplary embodiments, the applied energy generates fractionated thermal damage lesions in the skin in the selected direction, at block 206. In some embodiments, the fractionated thermal damage lesions are located a depth in a range of 0.5-5 mm, for example 0.5-2 mm, 1-4 mm, 2-5 mm or any intermediate, smaller or larger range of values from an epidermis or from a surface of the skin. In some embodiments, a distance between two adjacent thermal damage lesions is in a range between 0.1 mm to 5 mm, for example 0.1 mm to 0.5 mm, 0.2 mm to 1 mm, 0.5 mm to 2 mm, 1 mm to 3 mm, 2 mm to 5 mm, or any intermediate, smaller or larger range of values. In some embodiments, the fractionated thermal damage lesions comprises denatured collagen fibers. In some embodiments, the collagen fibers are denatured in the thermal damage lesions in a percentage range between 2% to 60%, for example 2% to 10%, 5% to 30%, 15% to 50%, 20% to 55% or any intermediate, smaller or larger range of values.

According to some exemplary embodiments, tension vectors are formed in the selected direction, at block 208. In some embodiments, the tension vectors are formed, for example by the immediate shrinkage of the collagen fibers, and/or healing of the fractionated thermal damage lesions. In some embodiments, the tension vectors are formed in a direction that reduces an appearance of wrinkles, for example in a direction that flattens and/or smoothens the skin surface. In some embodiments, the tension vectors are formed at directions that are at an angle or is substantially perpendicular to existing wrinkles and/or existing skin tension lines.

Exemplary Effect on Tissue

According to some exemplary embodiments, generating spaced-apart thermal damage lesions in deep layers of the skin leads to skin tightening, for example tightening of the external surface of the skin or, as another example, tightening of the deep dermal layer. In some embodiments, controlling a direction of the thermal damage lesions generation allows, for example to direct the skin tightening along a desired direction. In some embodiments, generating thermal damage lesions at a direction that is at an angle or is substantially perpendicular to existing wrinkles and/or existing skin tension lines, smoothens the skin surface. As used herein, substantially perpendicular means an angle between 80 degrees and 100 degrees. Optionally, generating thermal damage lesions at a direction that is at an angle or is substantially perpendicular to existing wrinkles and/or existing skin tension lines reduces an appearance of the wrinkles, for example to a degree which is similar to an effect of a facelift procedure.

Figures 3A, 3B, 3C:
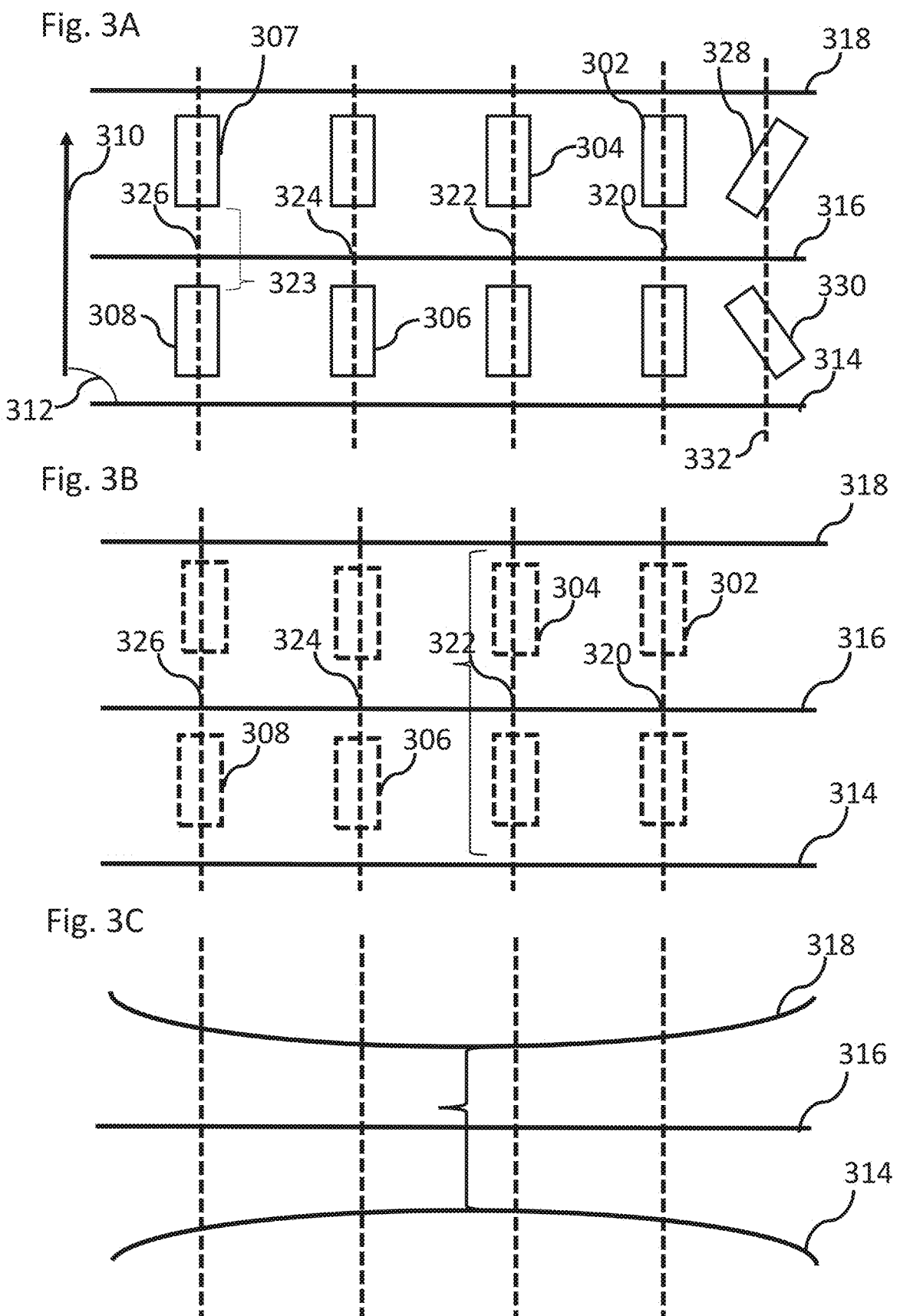
FIGS. 3A-3C are schematic illustrations showing skin tightening at a direction located at angle to skin relaxation lines, according to some exemplary embodiments of the invention.

Reference is now made to FIGS. 3A to 3C, depicting a directional skin tightening effect due to directional formation of thermal damage lesions, according to some exemplary embodiments of the invention.

According to some exemplary embodiments, for example as shown in FIG. 3A, energy emitted by one or more energy-emitting transducers, for example ultrasound transducers generate thermal damage lesions, for example lesions 302, 304, 306 and 308, in the skin. In some embodiments, the lesions 302, 304, 306 and 308 are formed at a depth in a range of 0.5-5 mm, for example 0.5-2 mm, 1-4 mm, 2-5 mm or any intermediate, smaller or larger range of values from an epidermis layer of the skin, or from a surface of the skin.

According to some exemplary embodiments, the lesions 302, 304, 306 and 308 are formed at a direction 310 that is in an angle 312 relative to at least one of the existing skin tension lines 314, 316 and 318. In some embodiments, angle 312 is about 90 degrees. In some embodiments, angle 312 is at least 45 degrees, for example at least 50 degrees, at least 70 degrees, at least 80 degrees, or any intermediate, smaller or larger angle relative to at least one of the existing skin tension lines 314, 316 and 318. Optionally, direction 310 is substantially perpendicular to at least one of the existing skin tension lesions 314, 316 and 318.

According to some exemplary embodiments, lesions are formed along selected skin tension vectors, for example as described in FIG. 2. In some embodiments, the lesions 302, 304, 306 and 308 are formed along selected, for example predetermined, skin tension vectors 320, 322, 324 and 326, respectively. In some embodiments, at least one of the skin tension vectors 320, 322, 324 and 326, are selected to be in an angle relative to at least one of the existing skin tension lines 314, 316 and 318, for example as described above with respect to the angle 312 between the direction 310 and the existing skin tension lines. In some embodiments, two or more lesions along a selected skin tension vectors are aligned relative to each other. Alternatively, lesions along a selected skin tension vector are positioned at an angle relative to each other, for example lesions 328 and 330 formed along a selected skin tension vector 332. In some embodiments, lesions along a selected skin tension vector are positioned at an angle of at least 45 degrees, for example at least 50 degrees, at least 70 degrees, at least 80 degrees, or any intermediate, smaller or larger angle relative to each other.

According to some exemplary embodiments, a distance 323 between adjacent lesions formed along a selected skin tension vector, for example lesions 307 and 308 is in a range of 0.1 mm to 5 mm, for example 0.1 mm to 0.5 mm, 0.2 mm to 1 mm, 0.5 mm to 2 mm, 1 mm to 3 mm, 2 mm to 5 mm, or any intermediate, smaller or larger range of values.

According to some exemplary embodiments, for example as shown in FIG. 3B, during a healing process of the lesions, collagen fibers and/or elastin fibers are generated within the lesions, which increase the contraction of the skin, for example when compared to pre-treatment conditions. In some embodiments, increasing skin contraction along desired, optionally selected, skin tension vectors, generates skin tightening along the skin tension vectors, for example as shown in FIG. 3C. In some embodiments, while collagen fibers and/or elastin fibers are formed deep inside the skin tissue, the skin tightening is visible on the skin surface, for example as bending of the existing skin tension lines.

Reference is now made to FIG. 4A, depicting skin tightening relative to existing aligned collagen fibers, according to some exemplary embodiments of the invention.

According to some exemplary embodiments, an applicator, for example ultrasound applicator 402 comprises at least one, for example 2, 3, 4, 5, 6, 7, 8, 9, 10 or any larger number of energy transmitting transducers, for example ultrasound transducers 404 and 406. In some embodiments, the ultrasound transducers 404 are elongated transducers, for example have a long axis and a short axis. Optionally, the ultrasound transducers have an elongated energy emitting surface, for example an energy emitting surface that has a long axis and a short axis. Alternatively, the ultrasound transducers are non-elongated transducers and/or have a non-elongated energy-emitting surface.

According to some exemplary embodiments, the at least one transducer, for example ultrasound transducers 404 and

406 emit energy, for example ultrasound energy 408 into skin tissue 410. In some embodiments, the ultrasound transducers 404 and 406 emit ultrasound energy, for example to generate at least one elongated thermal damage lesion in deep layers of the skin tissue 410. In some embodiments, the at least one elongated thermal damage lesion, for example lesion 412 having a long axis and a short axis, is generated by at least one elongated transducer or by a transducer having an elongated energy emitting surface. Alternatively, or additionally, the lesion 412 is generated by moving the applicator 402 in direction 414.

According to some exemplary embodiments, the elongated thermal damage lesion 412 is formed at an angle relative to an elongated axis of collagen fibers, for example axis 416 of collagen fiber 418. Optionally, the lesion 412 is substantially perpendicular to the axis 416. In some embodiments, the applicator 402 moves in direction 414 and is activated intermittently, for example to generate a series of spaced-apart thermal damage lesions, for example lesions 420 and 422, separated by non-damaged tissue or tissue that was not damaged in the same level as tissue in lesions 420 and 422. In some embodiments, the series of spaced-apart thermal damage lesions is aligned along a selected skin tension vector 426.

According to some exemplary embodiments, for example as shown in FIG. 4C, during a healing process, collagen and/or elastin grow within the spaced-apart lesions 420 and 422, for example to generate contraction along the selected skin tension vector 426.

Exemplary System

Reference is now made to FIGS. 5A-C, depicting a system for delivery of skin treatment, for example cosmetic skin treatments, according to some exemplary embodiments of the invention.

According to some exemplary embodiments, a system for delivery of skin treatments, for example system 502 comprises a control unit 504, and an ultrasound applicator 506 functionally coupled to the control unit 504. In some embodiments, the system 502 is configured to deliver skin tightening treatments, for example directional skin tightening treatments. In some embodiments, system 502 is similar or includes one or more components of the ultrasound system described in International Patent Application Publication No. WO2017212489A2.

According to some exemplary embodiments, the ultrasound applicator 506 comprises at least one, for example 2, 3, 4, 5, 6, 7, 8 9, 10 or any larger number of ultrasound transducers, for example ultrasound transducers 508. In some embodiments, at least some of the ultrasound transducers 508 are elongated ultrasound transducers having a long axis and a short axis. Optionally, at least some of the ultrasound transducers 508 comprise an elongated energy emitting surface having a long axis and a short axis. In some embodiments, the ultrasound transducers are arranged next to each other in the applicator, with optionally a long axis of all the transducers 508 in parallel.

According to some exemplary embodiments, each ultrasound transducer of transducers 508 is an elongated ultrasound transducer, optionally shaped as a rectangle. In some embodiments, the ultrasound transducer has at least one major axis and at least one minor axis. In some embodiments, a size of each ultrasound transducer or of an energy emitting surface of the transducer is in a range between 1 mm on 1.1 mm to 1 mm on 10 mm, for example 1 mm on 3 mm, 1 mm on 5 mm, 1 mm on 6 mm, or any intermediate, smaller or larger values.

According to some exemplary embodiments, the ultrasound transducers are arranged side by side in the applicator 506, in at least one row. Optionally the ultrasound transducers are arranged side by side in the applicator in two or more spaced-apart rows that are optionally parallel to each other. Optionally, the rows are distributed in a direction which is in parallel to a long axis of at least some of the ultrasound transducers 508. In some embodiments, each of the ultrasound transducers is configured to emit unfocused energy 510 or focused ultrasound energy into a skin tissue of patient 512, for example as described in International Patent Application Publication No. WO2017212489A2.

According to some exemplary embodiments, the control unit 504 comprises memory 514 which stores values of activation parameters of the ultrasound transducers and/or at least one treatment program. In some embodiments, the at least one treatment program is a planned treatment program personalized for a specific subject, for example patient. In some embodiments, the at least one treatment protocol comprises information regarding location of existing skin tension lines and/or location of at least one selected skin tension vector. Optionally, the memory includes information regarding the position of the existing skin tension lines and/or the at least one selected skin tension vector, personalized to a specific subject, for example relative to a coordinate system or landmarks of the subject.

According to some exemplary embodiments, the control unit 504 comprises a control circuitry 516 functionally connected to the memory 514 and to the ultrasound transducers 508. In some embodiments, the control circuitry 516 is configured to activate the ultrasound transducers according to activation parameter values stored in the memory 514 or according to an at least one treatment program stored in the memory 514.

According to some exemplary embodiments, the applicator 506 comprises at least one orientation and/or position sensor 518, functionally coupled to the control circuitry 516. In some embodiments, the at least one sensor 518 comprises a gyroscope and/or an accelerometer. In some embodiments, the control circuitry 516 is configured to identify a position and/or orientation of the ultrasound applicator 506 relative to at least one of, anatomical landmarks of the patient, a coordinate system applied on the patient 512, at least one existing skin tension line on the patient, and at least one selected skin tension vector, based on signals received from the at least one sensor 518. Alternatively or additionally, the control circuitry 516 is configured to identify a position and/or orientation of one or more of the ultrasound transducers 508 and/or a group of ultrasound transducer, relative to at least one of, anatomical landmarks of the patient, a coordinate system applied on the patient 512, at least one existing skin tension line on the patient, and at least one selected skin tension vector, based on signals received from the at least one sensor 518.

According to some exemplary embodiments, the control circuitry 516 processes the signals received from the at least one sensor 518, optionally using an alignment module 520, to determine if the ultrasound applicator 506 and/or the transducers 508 are at a target position and/or a target orientation of the stored treatment program. In some embodiments, the control circuitry 516 determines a relation between the signals received from the sensor 518 and the treatment program stored in the memory 514, optionally using the alignment module 520.

According to some exemplary embodiments, the control unit 504 comprises a user interface, for example user interface 522, functionally connected to the control circuitry 516.

In some embodiments, the user interface 522 is configured to generate and deliver a human detectable indication, for example an audio signal and/or a visual signals. In some embodiments, the user interface 522 comprises a display and/or at least one speaker.

According to some exemplary embodiments, the control circuitry 516 signals the user interface 522 to generate and deliver the human detectable indication according to a determined position and/or orientation of the ultrasound applicator or transducers relative to a target position and/or orientation in the stored treatment program. In some embodiments, a first human detectable indication is generated and delivered by the user interface 522 if the determined position and/or orientation is according to a target position and/or orientation of the stored treatment program. Additionally, the user interface 522 generates and delivers a second human detectable indication if the determined position and/or orientation is not according to a target position and/or orientation of the stored treatment program. Optionally, the user interface 522 generates and delivers instructions to a user of the system 502 how to move and/or turn the applicator 506 in order to reach the target position and/orientation. Alternatively or additionally, the user interface 522 generates and delivers instructions to a user of the system 502 how to move and/or turn the transducers 508 in order to reach the target position and/orientation.

According to some exemplary embodiments, the system 502 optionally comprises a marker 524 functionally connected to the control circuitry 516, configured to mark predetermined, for example planned or selected skin tension vectors on a skin of the patient 512. In some embodiments, the marker comprises one or more LED or laser, configured to mark with light the predetermined skin tension vectors on the body, for example on the face and/or neck, of the patient 512.

Additionally or alternatively, the marker 524 is configured to mark locations in the skin in which energy, for example ultrasound energy, was delivered. In some embodiments, the marker 524 is part of the applicator 506, and optionally comprises a non-permanent, for example an erasable ink for marking the skin of the subject.

According to some exemplary embodiments, the system 502 optionally comprises or is functionally connected to a printer 526. In some embodiments, the printer 526 is configured to print marking, for example markings indicating predetermined skin tension vectors on a mask, for example a gel mask. Optionally, the printer 526 is configured to generate the mask. In some embodiments, the gel mask comprises a face mask shaped and sized to be placed on a face of a subject, and to show the predetermined skin tension vectors to a user of the device. In some embodiments, the printer 526 is used to generate personalized gel masks for a specific patient and/or for a specific treatment program.

According to some exemplary embodiments, the system 502 comprises a cooling module 528 in the control unit 504, functionally coupled to the applicator 506, for example as described in International Patent Application Publication No. WO2017212489A2. In some embodiments, the cooling module 528 is configured apply cold through a skin contacting surface of the applicator 506, for example through the ultrasound transducers 508 to a surface of the skin. In some embodiments, the cooling module 528 is configured to apply cold, for example by optionally cooling the ultrasound transducers. In some embodiments, the cooling module 528 is configured to apply cold through the applicator 506 while emitting ultrasound energy into the skin tissue, for example to prevent damage to the skin surface contacting the applicator during the ultrasound energy emitting. In some embodiments, the system 502 cools a surface of the skin contacting the ultrasound transducers 508 and/or the applicator 506 for example as described in International Patent Application Publication No. WO2017212489A2.

According to some exemplary embodiments, the applicator comprises at least one thermoelectric cooler (TEC) functionally coupled to the cooling module 528 and the ultrasound transducers 508, and configured to cool at least some of the ultrasound transducers, for example as described in International Patent Application Publication No. WO2017212489A2.

According to some exemplary embodiments, the applicator 506 comprises at least one alignment marking, configured to indicate an orientation of the ultrasound transducers, for example a relative orientation of the ultrasound transducers. In some embodiments, the at least one alignment marking is a visual marking located within a field of view (FOV) of a user holding the applicator. In some embodiments, the visual marking allows the user to determine an orientation of ultrasound transducers that are located outside the FOV of the user, for example on or near a skin contacting surface of the applicator.

According to some exemplary embodiments, the applicator 506 comprises at least one user interface 521, functionally coupled to the control circuitry 516. In some embodiments, the user interface is configured to deliver one or more human detectable indications, for example audio and/or visual indications to a user holding the applicator 506. In some embodiments, the user interface 521 comprises at least one light emitting diode (LED) and/or at least one speaker for delivery of the human detectable indication. Alternatively or additionally, the user interface 521 comprises at least one user input receiver, for example at least one button, configured to receive at least one input signal from a user holding the applicator. In some embodiments, the at least one user input signal comprises an activation signal.

According to some exemplary embodiments, a housing of the applicator 506 is at least partly transparent, for example to allow visualization of a contact point between the ultrasound transducer and the skin, and/or one or more markings on the skin, by a user holding the applicator 506.

Exemplary Transducers Arrangement

Reference is now made to FIGS. 5B and 5C depicting different transducers arrangements on an emitting surface of an applicator, according to some exemplary embodiments of the invention.

According to some exemplary embodiments, a plurality of ultrasound transducers, for example transducers 530 and 532 are arranged in one or more rows on, or close to an emitting surface of an applicator 534. Optionally, the transducers are elongated transducers, having a long axis 538 and a short axis 537. In some embodiments, ultrasound transducers in a row, for example transducers 530 and 532, are arranged side by side, optionally positioning a long axis 538 of each transducer in parallel to other transducer in the row. In some embodiments, one or more rows of ultrasound transducers comprise 3, 4, 5, 6, 7, 8, 9 or any smaller or larger number of transducers. In some embodiments, a distance between adjacent transducers in a row, for example transducers 532 and 536 is in a range between 0.5 mm to 3 mm, for example 0.5 mm to 1 mm, 0.7 mm to 2 mm, 1.5 mm to 3 mm or any intermediate, smaller or larger distance. In some embodiments, a minimal distance between two adjacent transducers in different rows, for example transducers 530 and 532 is in a range between 0.5 mm to 3 mm, for example 0.5 mm to 1 mm, 0.7 mm to 2 mm, 1.5 mm to 3 mm or any intermediate, smaller or larger distance.

According to some exemplary embodiments, a length 540 of each transducer is in a range between 1 mm to 10 mm for example, 1 mm to 5 mm, 2 mm to 7 mm, 4 mm to 8 mm, 6 mm to 10 mm or any intermediate, smaller or larger range of values. In some embodiments, a width 542 of each transducer is in a range between 0.1 mm to 5 mm, for example 0.1 mm to 2 mm, 1 mm to 4 mm, 2 mm to 5 mm or any intermediate, smaller or larger range of values.

According to some exemplary embodiments, for example as shown in FIG. 5C, some of the ultrasound transducers of an applicator 533, for example transducers 544 and 546 in the same row are tilted at an angle in a range between 2 degrees to 90 degrees, for example at an angle between 10 degrees and 50 degrees, at an angle between 30 degrees and 60 degrees, or any intermediate, smaller or larger range of values. Optionally, transducers in different rows, for example transducers 548 and 550, are tilted relative to each other, at an angle between 10 degrees and 50 degrees, at an angle between 30 degrees and 60 degrees, or any intermediate, smaller or larger range of values.

Exemplary Skin Tightening Treatment

According to some exemplary embodiments, a subject, for example a patient is diagnosed prior to a skin tightening treatment, for example to determine whether a global skin tightening effect is required, for example as in a facelift procedure, or a local effect is required, for example to locally treat one or more specific wrinkles. In some embodiments, a treatment plan is generated and optionally includes one or more treatment sessions. As used herein, a treatment session is a treatment meeting that ends with the release of the subject from the clinic after the treatment session or the treatment has been completed. In some embodiments, a treatment plan optionally includes several treatment sessions.

Figure 6A:
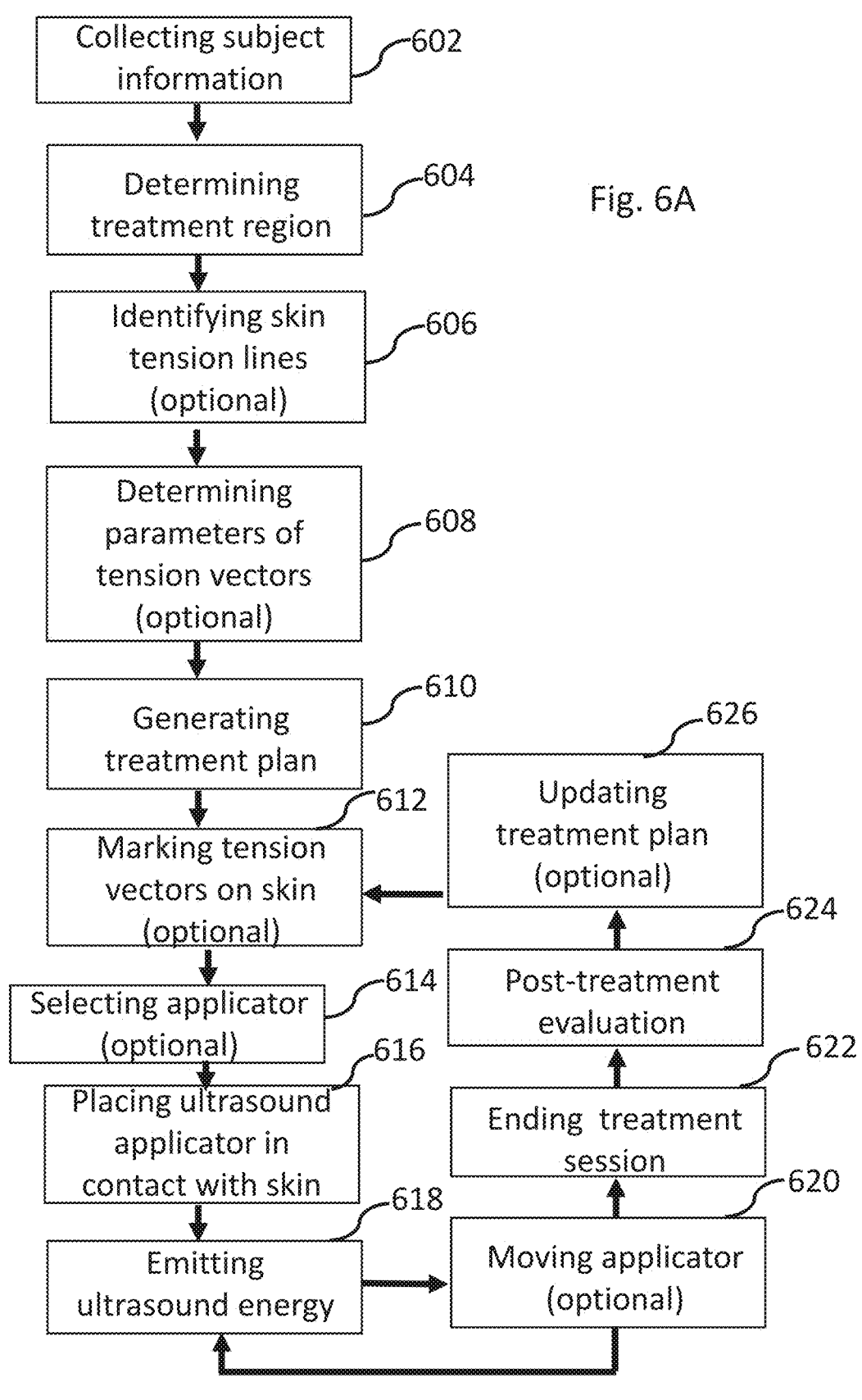
FIG. 6A is a flow chart describing actions performed by a user of the skin tightening system during a process for generating directional tension vectors, according to some exemplary embodiments of the invention.

Reference is now made to FIG. 6A depicting a skin tightening process, according to some exemplary embodiments of the invention.

According to some exemplary embodiments, information on a subject that intends to undergo a skin tightening process is collected at block 602. In some embodiments, the collected information includes at least one of, medical history of the subject, information regarding skin elasticity in a specific region of interest (ROI), depth of one or more wrinkles in the ROI, and/or density of wrinkles in the ROI.

According to some exemplary embodiments, a treatment region is determined at block 604. In some embodiments, the treatment region is determined based on the information collected at block 602. In some embodiments, determining a treatment region comprises determining if a global skin tightening process is required or a local skin tightening process is required, based on the size of the treatment region. In some embodiments, a global skin tightening process is required if an area of the treatment region is larger than 12 cm², for example larger than 20 cm², larger than 25 cm², larger than 30 cm², or any intermediate, smaller or larger treatment region area.

According to some exemplary embodiments, relaxed skin tension lines are optionally identified, at block 606. In some embodiments, the relaxed skin tensions lines are identified in the determined treatment region or in the vicinity of the region, for example at a distance of up to 10 cm, up to 5 cm, up to 2 cm, or any intermediate, smaller or larger value from the determined treatment region. In some embodiments, the identified skin tension lines comprise at least one of, Langer's lines, Cox's lines, Kraissel's lines, Rubin's lines, Straith's lines, Bulacio's lines, and RSTL. In some embodiments, the relaxed skin tension lines are identified using visualization techniques, for example using an optic sensor or a camera. Alternatively or additionally, the relaxed skin tension lines are identified by touching or pinching the skin.

According to some exemplary embodiments, values of one or more parameters of tension vectors, for example planned tension vectors to be formed by the skin tightening treatment, are optionally determined at block 608. In some embodiments, the tension vectors parameters comprise, direction of tension vectors, location of tension vectors, width of tension vectors, length of tension vectors, and/or shape of tension vectors. In some embodiments, the parameter values of planned tension vectors are determined relative to at least some of the skin tension lines identified at block 606. In some embodiments, the direction of the planned tension vectors is determined based on a requited skin tightening effect, whether the required effect is a global effect, for example to generate a facelift, or the required effect is a local effect, for example to minimize an appearance of one or more specific wrinkles.

According to some exemplary embodiments, a treatment plan is generated at block 610. In some embodiments, the generated treatment plan comprises a number of treatment sessions, and/or values of the one or more parameters optionally determined at block 608. In some embodiments, the generated treatment plan comprises parameter values of a treatment, for example an ultrasound treatment, for treating the determined treatment region.

According to some exemplary embodiments, the treatment parameter values comprise at least one of, type of ultrasound applicator, number of ultrasound transducers, arrangement of the ultrasound transducers, energy emitting time along the predetermined tension vectors, and/or duration of rest periods in which energy is not emitted into the skin during a treatment session and/or between treatment sessions. In some embodiments, the type of ultrasound applicator is based on a shape and size of an ultrasound applicator, for example a shape and size of a skin contacting surface of the ultrasound applicator. In some embodiments, an arrangement of the ultrasound transducers comprise a distance between adjacent ultrasound transducers, number of ultrasound transducers in a row, number of rows, and/or an angle between adjacent ultrasound transducers. In some embodiments, different treatment parameter values ac needed for a global treatment and for a local treatment. Alternatively or additionally, the treatment parameter values are based on at least one of, a size of the treatment region, location of the treatment region, and/or the determined parameter values of tension vectors.

In some embodiments, the generated treatment plan includes information regarding a number of treatment sessions needed to reach a target effect, for example a desired effect, in a specific subject. Additionally, the generated treatment plan includes information regarding interval duration between consecutive treatment sessions, number of locations in the skin to be treated in each treatment session, duration of each treatment session, and energy delivery duration at each treatment location.

According to some exemplary embodiments, planned tension vectors are optionally marked on the skin, at block 612. In some embodiments, the planned tension vectors are optionally marked on the skin using the marker 524 shown in FIG. 5A. Alternatively, a mask, for example a gel mask, which includes the planned tension vectors is prepared, for example using the printer 526 shown in FIG. 5A. Optionally marking on the skin comprises attaching a sticker to the skin.

According to some exemplary embodiments, an applicator, for example an ultrasound applicator, is optionally selected at block 614. In some embodiments, the applicator is selected based on the size and/or shape of a skin contacting surface of the applicator. Alternatively or additionally, the applicator is selected based on a number of ultrasound transducers and/or arrangement of ultrasound transducers in the applicator. Alternatively or additionally, the applicator is selected based on the determined parameters of the tension vectors, for example to allow the formation of the tension factors having parameter values as determined at block 608.

According to some exemplary embodiments, the applicator is placed in contact with the skin, at block 616. In some embodiments, an emitting surface of at least some ultrasound transducers is placed in contact or close to a skin surface, for example at a distance smaller than 3 cm, smaller than 2 cm, smaller than 1 cm, or any intermediate, smaller or larger distance from the skin surface. In some embodiments, the applicator is placed in a location previously determined in the treatment plan. Optionally, the applicator is placed in contact with the skin at the determined treatment region. In some embodiments, the applicator and/or the transducers are placed in a predetermined orientation relative to one or more planned tension markers, optionally marked on the skin.

According to some exemplary embodiments, ultrasound energy, is emitted, at block 618. In some embodiments, the ultrasound energy is emitted by one or more of the ultrasound transducers of the applicator towards skin tissues. In some embodiments, the emitted ultrasound energy is a non-converging, also termed herein as unfocused, ultrasound energy. In some embodiments, the skin surface is cooled by the applicator prior to and/or during the emitting of the ultrasound energy. In some embodiments, the ultrasound energy is emitted for a time period optionally selected by the user of the system. Alternatively, the ultrasound energy is emitted for a time period previously determined as part of the generated treatment plan. In some embodiments, the ultrasound energy is emitted when the applicator and/or the transducers are positioned at the first location.

According to some exemplary embodiments, the applicator is optionally moved to a different location, for example to a second location, at block 620. In some embodiments, once the applicator is at the second location, ultrasound energy is emitted, for example as described at block 618. In some embodiments, the first and second locations, are locations along the planned tension vectors.

According to some exemplary embodiments, the applicator is moved by the user, from the first location to other locations along a path of a planned tension vector. In some embodiments, when the applicator is located at a target location along the path, energy is emitted, for example as described at block 618. In some embodiments, the applicator is moved from a first location to an adjacent location on the path. Alternatively, the applicator is moved between remote, non-adjacent locations on the path.

Optionally, a movement pattern of the applicator along the path is predetermined, and is optionally part of the generated treatment plan. In some embodiments, the applicator movement pattern is determined according to a response of the tissue at a specific location to the applied ultrasound energy, for example if a cooling period is required after treating a first location then the applicator is moved to a remote location to continue with the treatment session.

According to some exemplary embodiments, the applicator is rolled over the skin surface between treatment locations. Alternatively, the applicator is detached from the skin surface at a first treatment location, and is attached to the skin surface at a second treatment location.

According to some exemplary embodiments, a treatment session ends at block 622. In some embodiments, the treatment session ends after finishing ultrasound energy application to skin tissue at specific locations included in the treatment session, and/or as included in the generated treatment plan.

According to some exemplary embodiments, post-treatment evaluation is performed, at block 624. In some embodiments, the post-treatment evaluation is performed in order to evaluate a condition of the skin tissue following the treatment. In some embodiments, the post-treatment evaluation is performed at the end of each treatment session. Alternatively or additionally, the post treatment evaluation is performed during a treatment session, for example after the emitting of ultrasound energy to a specific treatment location.

According to some exemplary embodiments, the treatment plan is optionally updated, at block 626. In some embodiments, the treatment plan is updated based on the post treatment evaluation. In some embodiments, if the effect following the treatment session is not sufficient, then ultrasound energy delivery at one or more previous locations is repeated. In some embodiments, if a longer recovery is needed in a specific treated region, then a remote treatment location is selected for the next treatment session. Optionally, new tension vectors are determined based, for example, on the results of the post-treatment evaluation. For example, if the post-treatment evaluation indicated that an effect following the treatment is not sufficient, then new tension vectors are determined.

According to some exemplary embodiments, a new treatment session starts according to the generated treatment plan or optionally an updated treatment plan. Alternatively, a treatment session is repeated, for example according to the updated treatment plan.

Figure 6B:
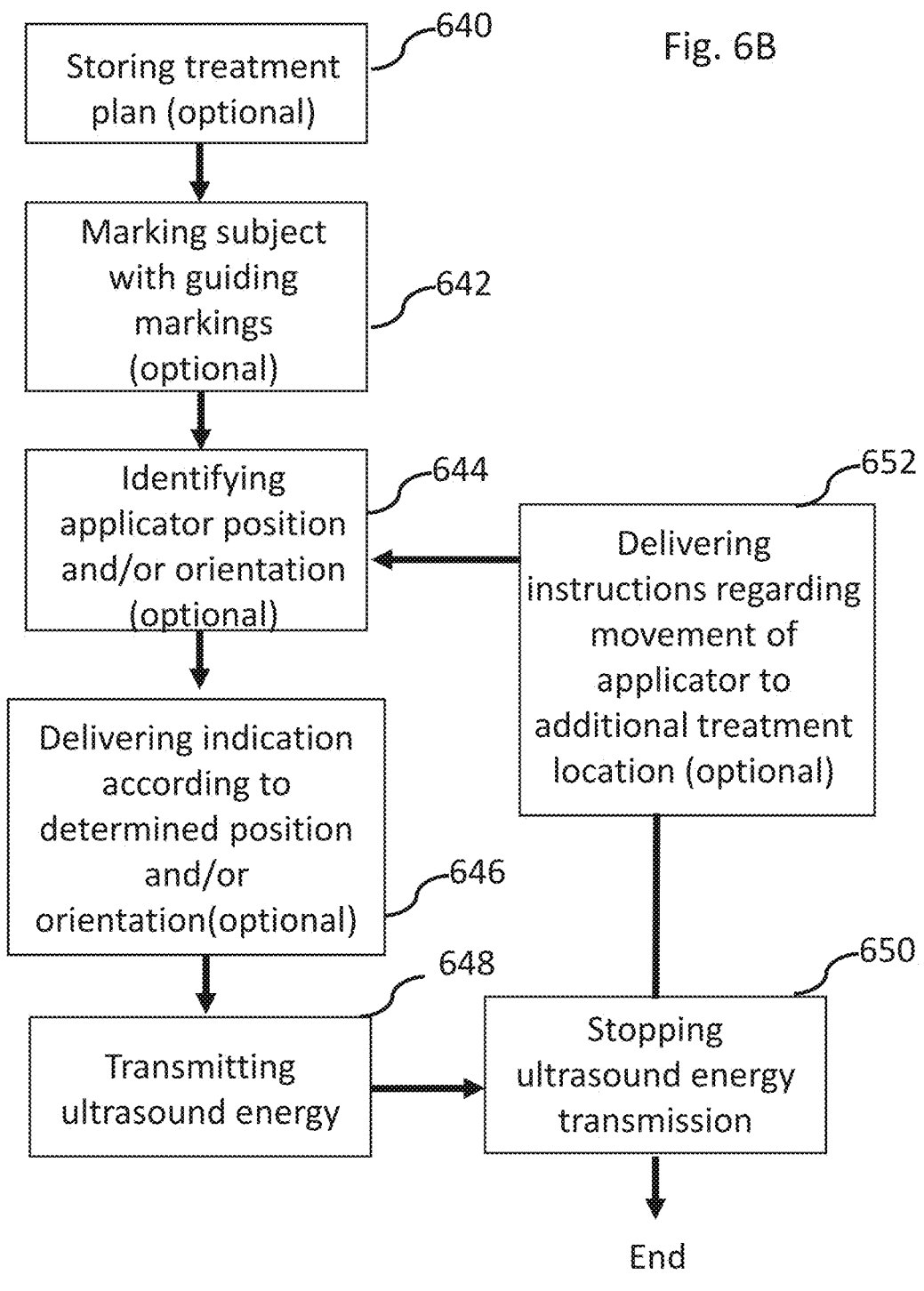
FIG. 6B is a flow chart describing actions performed by the skin tightening system during a process for generating directional tension vectors, according to some exemplary embodiments of the invention.

Reference is now made to FIG. 6B, describing activities performed by a skin tightening system, for example system 502 shown in FIG. 5A, according to some exemplary embodiments of the invention.

According to some exemplary embodiments, a treatment plan is optionally stored in a memory of the system, for example memory 514 shown in FIG. 5A. In some embodiments, the stored treatment plan is the treatment plan generated at block 610 of FIG. 6A.

According to some exemplary embodiments, the system optionally marks a skin surface of a subject with guiding markings, at block 642. In some embodiments, the guiding markings optionally indicate a location of planned tension vectors. Alternatively or additionally, the guiding markings optionally indicate one or more treatment locations for placing the ultrasound applicator in contact with the skin. In some embodiments, the guiding markings are optionally applied, for example projected, on the skin surface of the subject.

According to some exemplary embodiments, the system optionally identifies a position and/or an orientation of the ultrasound applicator, at block 644. In some embodiments, the system identifies the position and/or orientation of the applicator based on signals received from at least one sensor of the applicator, for example a gyroscope and/or an accelerometer. Alternatively or additionally, the system identifies a position and/or an orientation of the ultrasound applicator by receiving signals from at least one optic sensor, for example a camera, functionally connected to a control unit of the system.

According to some exemplary embodiments, the system optionally identifies a position and/or orientation of the applicator relative to specific landmarks on the body of the subject, relative to planned tension vectors, and/or relative to the guiding markings.

According to some exemplary embodiments, the system optionally delivers an indication regarding the determined position and/or orientation of the applicator, at block 646. In some embodiments, the indication is a human detectable indication, for example an audio and/or a visual indication. In some embodiments, the delivered indication comprises a first indication for indicating that the applicator is in a planned position and/or orientation, and a second indication for indicating that the applicator is not in the planned position and/or orientation.

According to some exemplary embodiments, ultrasound energy is transmitted at block 648. In some embodiments, the ultrasound energy is transmitted, optionally automatically, when the ultrasound applicator is in a planned position and/or orientation. Alternatively or additionally, the ultrasound energy is transmitted, optionally automatically, when the ultrasound applicator is at a target treatment location. Optionally, the ultrasound energy is transmitted when the system receives an activation signal from the user interface of the control unit, for example the user interface 522 shown in FIG. 5A or a user interface of the ultrasound applicator. In some embodiments, the system generates and delivers the ultrasound energy according to treatment parameter values stored in the memory, and/or according to at least one treatment plan stored in the memory.

According to some exemplary embodiments, the system stops the delivery of ultrasound energy at block 650. In some embodiments, the system stops the delivery of ultrasound energy automatically, for example according to treatment parameter values and/or at least one treatment plan stored in the memory. Alternatively, the system stops the delivery of ultrasound energy when receiving a signal from a user interface of the control unit or from a user interface of the applicator.

According to some exemplary embodiments, the system optionally delivers instructions regarding movement of the applicator to an additional treatment location, at block 652. In some embodiments, the system optionally delivers instructions for example using a map or a visual indication presented by the user interface of the control unit, or a user interface of the applicator. In some embodiments, the process continues, optionally as described at block 644, for example until a treatment session ends.

Exemplary Directional Tension Vectors on Facial Skin

According to some exemplary embodiments, the skin tightening procedure, allows generating an effect of a facelift procedure or a mini-facelift procedure in a non-invasive way. Reference is now made to FIGS. 7A-7D depicting treatment regions of an applicator on a face of a subject, according to some exemplary embodiments of the invention.

Figure 7A:
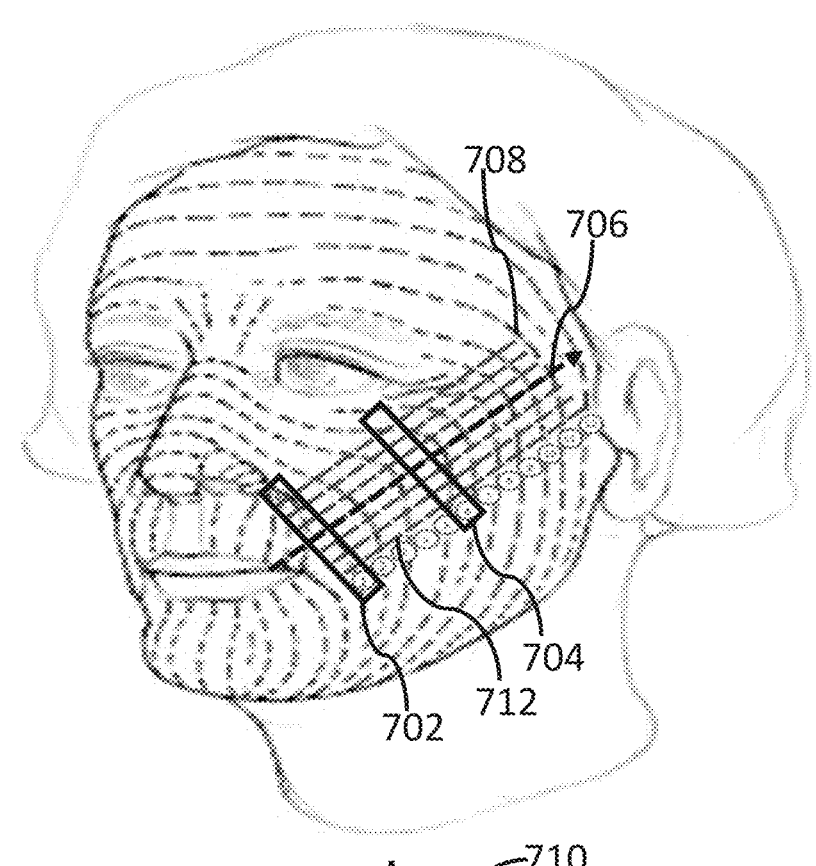
FIGS. 7A-7B are schematic illustrations showing ultrasound energy application patterns for creating directional collagen contraction and/or skin tightening using elongated transducers, according to some exemplary embodiments of the invention.
Figure 7B:
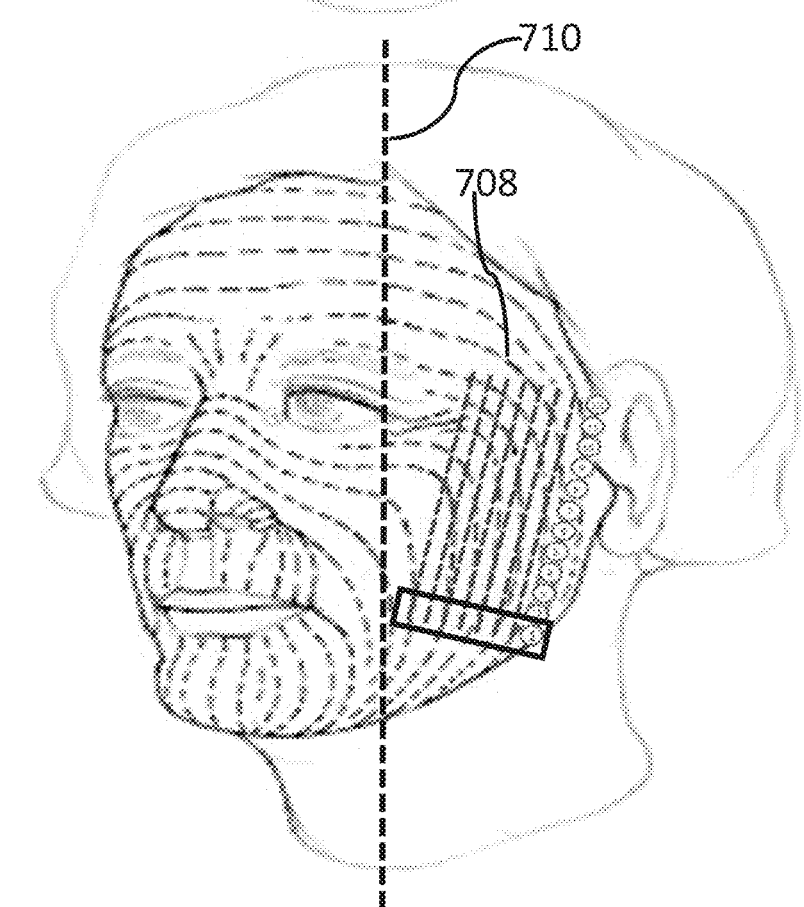

According to some exemplary embodiments, for example as shown in FIGS. 7A and 7B, elongated ultrasound transducers, each optionally having an elongated piezoelectric element, are moved on the skin between different treatment regions, for example treatment regions 702 and 704. In some embodiments, the elongated ultrasound transducers, for example 7 ultrasound transducers as shown in FIGS. 7A and 7B, are arranged side by side in a single row. In some embodiments, a skin-contacting surface of the applicator is placed in contact with the skin in a first treatment region, for example treatment region 702, and delivers ultrasound energy to skin tissue at the first treatment region 702. Then, the applicator is moved to additional treatment regions, for example treatment region 704, distributed along at least one planned tension vector 706 on a skin, for example face skin and/or neck skin of the subject.

According to some exemplary embodiments, a long axis of a rectangular shape of the elongated ultrasound transducer, for example a long axis of a rectangular piezoelectric element, is aligned with lines on the skin, for example the at least one planned tension vector 706, which are substantially perpendicular to skin tension lines 708, for example the RSTL lines. In some embodiments, the skin tightening treatment would consist of starting on one side of the face medially, and then perform adjacent ultrasound energy applications following a direction substantially perpendicular to skin tension lines, for example the RSTL lines. Optionally, the procedure will include application of ultrasound energy with or without more upward vertical components relative to a longitudinal axis 710 of the body, optionally depending on a treatment program for a specific patient, and/or a technique of the system user.

Optionally, the procedure could consist of performing two or more passes on each side of the face to create collagen shrinkage and skin tightening in directions substantially perpendicular to skin tension lines, for example the RSTL in at least one first pass, and more vertical direction in at least one additional pass, for example. Optionally, a method of treating the skin by applying these series of thermal injuries in skin could be a mix of these two principles, starting in the mid face in directions substantially perpendicular to the RSTL to then curve upward toward the lateral side of the face in a direction which is more vertical to the longitudinal axis 710 of the body. Optionally, the applied energy overlaps in one or more directions, but still produced to generally replicate the skin tightening and pulling effects of a facelift or mini-facelift.

According to some exemplary embodiments, for treatments of the lower face, the desired collagen shrinkage and skin tightening directions start from medial to lateral locations, these lines being substantially perpendicular to the RSTL lines shown in FIGS. 1B and 1n FIGS. 7A-7D. In some embodiments, for forehead treatments, as another examples, the desired collagen shrinkage and skin tightening directions are substantially parallel to the longitudinal axis 710 in order to create vertical lifting to treat the forehead wrinkles, and/or to create eyebrow lift for example. Optionally, these lines are substantially perpendicular to the RSTL lines in the forehead area, as shown in FIG. 1B and FIGS. 7A-7D.

FIG. 7A shows examples of application pattern to create lines of collagen contraction and skin tightening, according to some exemplary embodiments of the invention. In FIG. 7A, each rectangle represents a footprint of a 1×5 mm piezoelectric element of an ultrasound applicator. The 7 rectangles aligned along a short axis of a piezoelectric element represent the 7 transducers mounted in an applicator, for example a handpiece. The numbers from 1 to 12 represent the adjacent energy applications at different adjacent locations to create lines of collagen shrinkage and skin tightening in desired directions along the long axis of the elongated ultrasound transducers.

In some embodiments, for example as shown in FIG. 7A, the long axis of each piezoelectric element is generally aligned, for example at least 80% aligned, perpendicular to the RSTL lines, for example lines 708 to optionally create collagen shrinkage and lines of skin tightening substantially perpendicular to the RSTL lines.

In some embodiments, for example as shown in FIG. 7B ultrasound energy is applied when the long axis of the piezoelectric element is generally aligned in a more vertical manner, closer to a longitudinal axis 710 of the body, to create collagen shrinkage and skin tightening in a more vertical direction, for example to lift the skin upward and overcome an effect of gravity on sagging skin.

According to some exemplary embodiments, different forms of energy application are used to create vectors of collagen shrinkage and skin tightening. In some embodiments, focused ultrasonic energy is used to produce a cylindrical focal zone in tissue, for example thermal damage lesions. Alternatively, non-invasive or minimally invasive (such as microneedles for example), bipolar or unipolar elongated RF electrodes are used to generate the thermal damage lesions. Alternatively, systems using non-ablative lasers emitted in an elongated manner with respect to the skin surface, are used to deposit the energy in the dermal layer. Optionally, skin surface cooling methods are used to protect the superficial layers of the skin, which optionally includes the epidermis, the dermoepidermal junction, and/or the papillary dermis.

Figures 7C, 7D, 8:
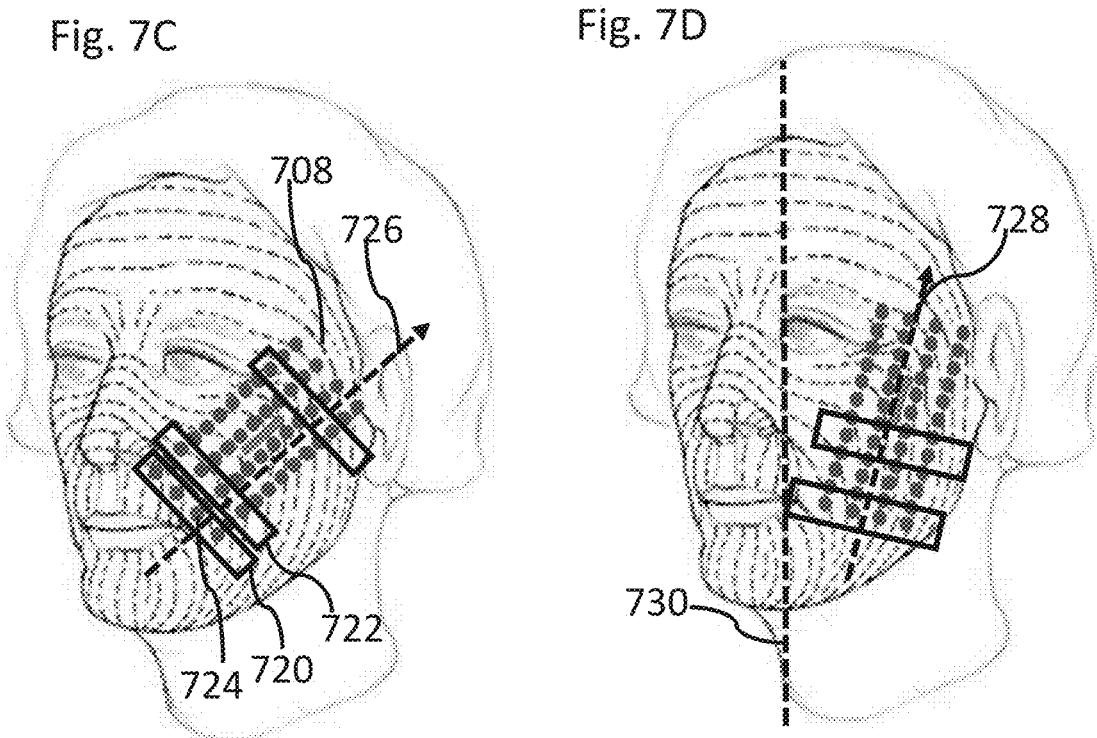
FIGS. 7C and 7D are schematic illustrations showing ultrasound energy application patterns for creating directional collagen contraction and/or skin tightening using non-elongated transducers, according to some exemplary embodiments of the invention.
FIG. 8 is a schematic illustration showing generation of curved tension vectors, according to some exemplary embodiments of the invention.

According to some exemplary embodiments, for example as shown in FIGS. 7C and 7D, non-elongated, optionally symmetrical transducers are used to create collagen shrinking and/or skin tightening in a desired direction. In some embodiments, non-elongated transducers each having a foot print 724, generate non-elongated fractionated thermal damage lesions in the skin. Optionally, moving an ultrasound transducer between treatment regions distributed along at least one desired tension vector 726 on a skin, generates collagen shrinking and/or skin tightening in a direction of the planned tension vector 726, by forming fractionated thermal damage lesions with optionally at least partly denatured collagen, along the planned tension vector 726. In some embodiments, a density of the fractionated thermal damage lesions generated by the non-elongated transducers, is higher in the direction of the planned tension vector 726.

According to some exemplary embodiments, for example as shown in FIG. 7C a direction of the planned tension vector 726 is generally aligned perpendicular to the RSTL lines 708 to create collagen shrinkage and lines of skin tightening perpendicular to the RSTL lines 708, for example as shown in FIG. 7A. In some embodiments, for example as shown in FIG. 7D, a direction of the planned tension vector 726 generated by the fractionated thermal damage lesions is more vertical and closer to a longitudinal axis 730 of the body, for example to generate an upward skin tightening effect to overcome an effect of gravity on sagging skin.

According to some exemplary embodiments, ultrasound energy is applied to generate fractionated thermal damage lesions at a Superficial Muscular Aponeurotic System (SMAS) layer. In some embodiments, to affect the SMAS layer, the energy-emitting transducers, for example ultrasound transducers are activated to generate thermal damage lesions along a vertical planned tension vector which is closer to a longitudinal axis 730 of the body, for example as shown in FIGS. 7B and 7D.

According to some exemplary embodiments, for example as shown in FIG. 8, the planned tension vector, to be generated by the fractionated thermal damage lesions is a curved line, for example to generate curved skin tightening.

Exemplary Simulations

General FEA Model Description

Simulations were performed to characterize the energy deposition of the Sofwave device in 3D in order to calculate the volume of denatured collagen, taking into consideration the edge effects due to the finite length of the PZT. In addition, the simulations were performed to calculate the expected collagen shrinkage in three orthogonal axes.

Figure 9:
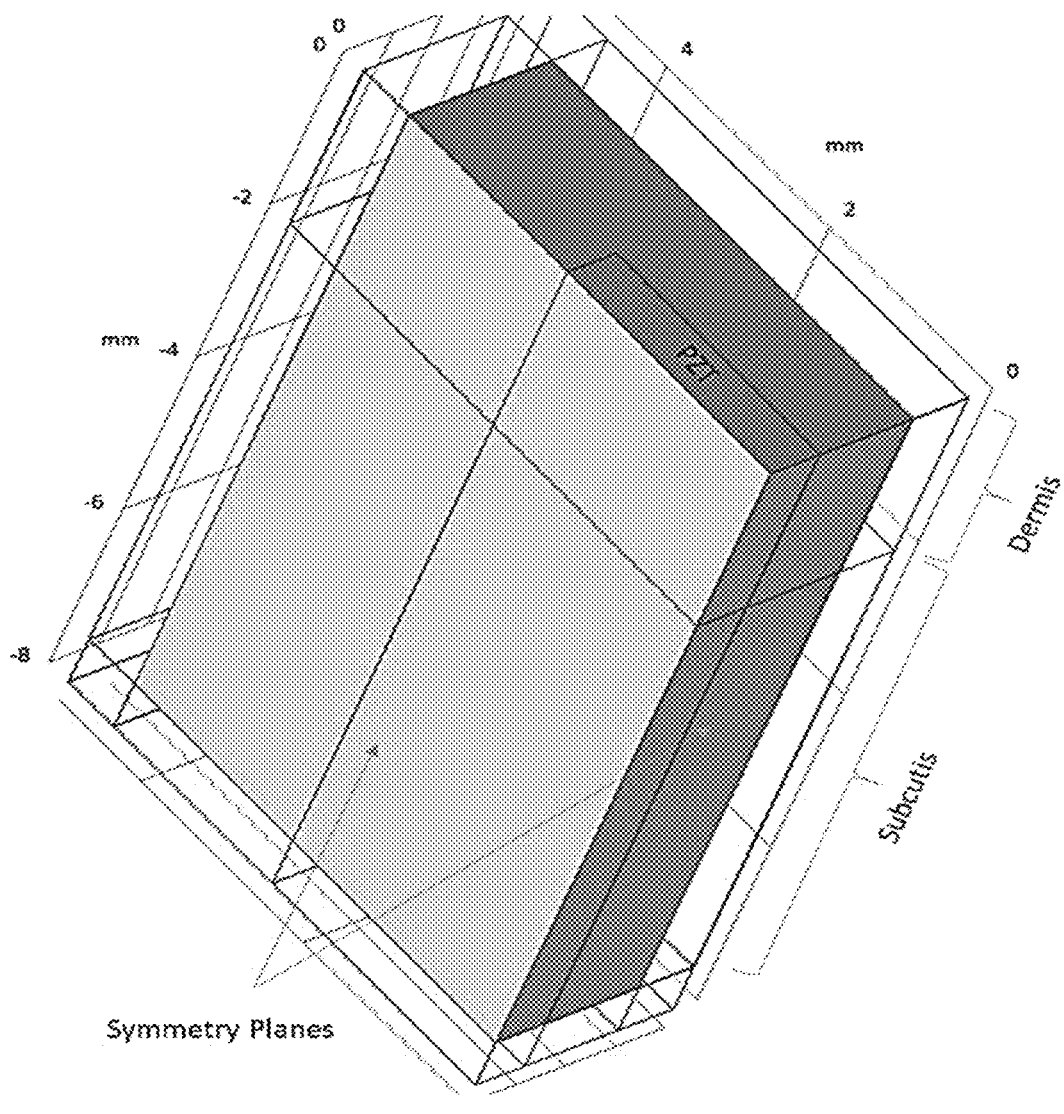
FIG. 9 is a schematic illustration of a 3D model geometry used in a simulation experiment.

A model used for the simulations was based on the geometry shown in FIG. 9. Only the dermis and subcutis layers were modeled to reduce the computational and memory requirements. Furthermore, only a quarter model was implemented with two symmetry planes to take advantage of the intrinsic symmetry associated with the model. The model is surrounded by Perfectly Matched Layers (PML) to absorb all remaining ultrasonic energy without producing any reflection.

The PZT was modeled by a rectangular surface with constant pressure. The first step was to model the acoustic energy deposition in the tissue layers. Following the acoustic simulation, the acoustic power deposited in tissue was used as an external source in the Heat Transfer module in order to calculate the thermal profile generated by the absorption of acoustic energy in the dermal and subcutaneous layers. Then, the thermal damage predicted by the Arrhenius equation was calculated using equation 1:

$$\Omega = A \cdot \int_0^t e^{-\left(\frac{E_A}{R \cdot T(\tau)}\right)} \partial \tau \qquad (1)$$

Where:

$\Omega$ is the thermal dose,

A is the frequency factor ($s^{-1}$), $E_A$ is the activation energy ($J \cdot mol^{-1}$)

R is the perfect gas constant ($8.314\ J \cdot K^{-1} \cdot mol^{-1}$), and

T is the temperature (K)

The acoustic and thermal properties involved with the simulations are listed in Table 1 below. For the acoustic properties, the values were taken at 11.5 MHz, which is the frequency used by the Sofwave console.

TABLE 1

|  | Characteristics | Dermis | Subcutis | Blood |
|---|---|---|---|---|
| Properties | Density (kg/m³) | 1109 | 1050 | 1060 |
|  | Perfusion rate (s⁻¹) | 1.25e-3 | 1e-4 | N/A |
| Acoustic | Speed of sound (m/s) | 1595 | 1478 | N/A |
|  | Attenuation (Np/cm) | 230 | 83 | N/A |
| Thermal | Thermal conductivity (W/m · K) | 0.37 | 0.19 | N/A |
|  | Heat capacity (J/kg · K) | 3391 | 2500 | 3770 |
| Arrhenius | Frequency factor (s⁻¹) | 1.14e86 | 2.19e124 | N/A |
|  | Activation energy (J/mol) | 5.62e5 | 7.78e5 | N/A |

To mimic the thermal effects of the proprietary embedded cooling system, the average temperature of the dermal surface interface during the ultrasound pulse was calculated as 15° C. using a cross-sectional 2D model, and applied as constant temperature condition on the PZT surface of FIG. 9.

The minimal and maximal mesh size of the model were set to 5.7E-3 and 5.7E-2 mm, respectively.

Tissue Temperature and Zones of Denatured Collagen—3D

Figure 10:
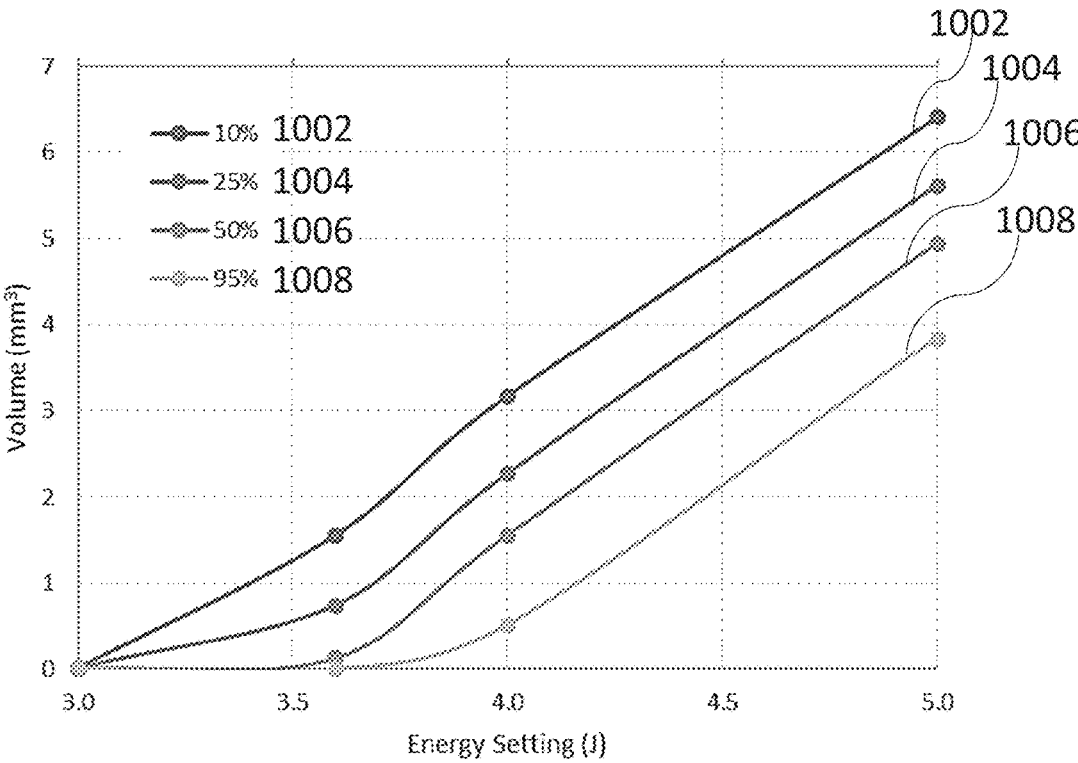
FIG. 10 shows volume of denatured collagen between 3 and 5 Joules (J), the curves represent the volume bounded by an iso-surface of the same percentage of collagen denaturation, as calculated using a simulation.

The temperature profiles for energy settings of 3, 4, and 5 J were simulated. Then, as stated above, thermal damage levels were calculated using equation 1, and the volumes bounded by iso-contour of 10, 25, 50, and 95% collagen denaturation generated, as shown in FIG. 10 [FIG. 10 shows volume of denatured collagen between 3 and 5 J. The curves represent the volume bounded by an iso-surface of the same percentage of collagen denaturation. The corresponding maximal dermal temperatures are shown on the top axis].

Figure 11:
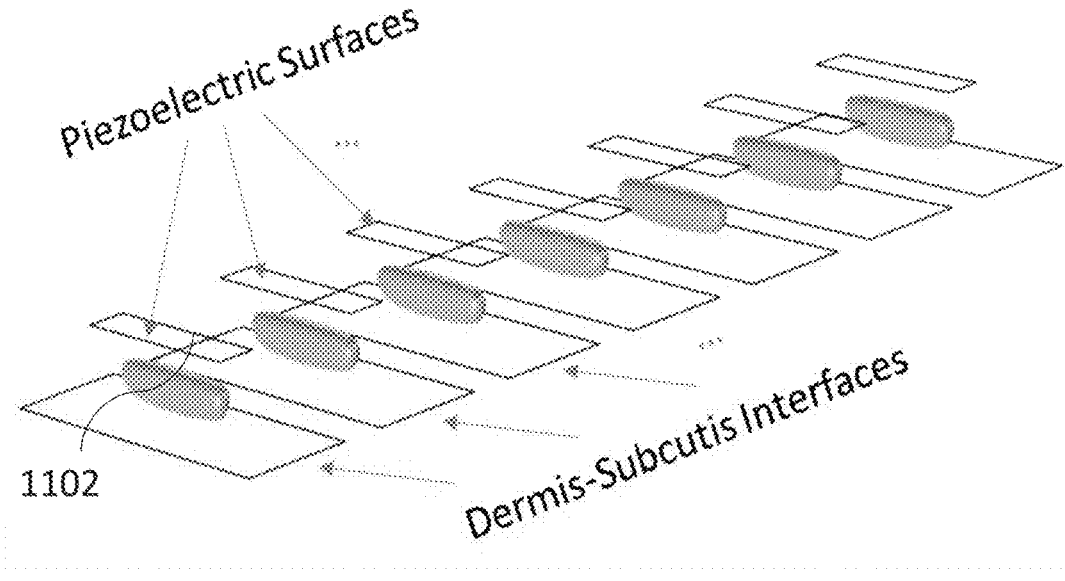
FIG. 11 shows volumes bounded by 10% collagen denaturation (in green), the simulation results were mirrored across two symmetry planes, and copied 7 times with a 4-mm distance between two adjacent PZT to replicate a design of the Sofwave handpiece, for example an applicator.

The volume bounded by the 10% denatured collagen is shown in FIG. 11 [FIG. 11 shows volumes bounded by the 10% collagen denaturation 1102 (in green)]. The simulation results were mirrored across the two symmetry planes, and copied 7 times with a 4-mm distance between two adjacent PZT to replicate the design of the Sofwave handpiece].

The center of the denatured zone was located at about 1.5 mm underneath the skin surface and entirely located in the dermal layer. The zone has a quasi-elliptical 3D shape completely surrounded by non-denatured collagen, being therefore fractional by definition. The cooling system of the handpiece insured a zone of non-denatured collagen above the denatured zones, up to the dermal surface level.

Collagen Contraction

The collagen molecule consists of triple helical tropocollagen molecules of about 300 nm long, and 1.5 nm in diameter. Staggered arrays of collagen molecules form fibrils, which arrange to form collagen fibers. Like other biological proteins, collagen can denature when heated. During the denaturation process, the triple helix structure progressively changes its 3D conformational configuration by breaking of different cross-links present at the intermolecular level such as the nonenzymatic glycosylation of lysine and hydroxylysine residues and at the intramolecular level such as the disulphide bridges. These complex phenomena result in length reduction, or shrinkage. When the collagen concentration in tissue is high such as in skin, the resulting effect is an overall tissue shrinkage. This phenomenon could be used, and is used in some embodiments of the invention, for non-invasive or minimally invasive skin tightening procedures, and/or to mimic facelift procedures where plastic surgeons usually pull the skin generally in the direction of the "Lines of Maximal Extensibility" (LME) in order to soften or remove facial wrinkles which are generally located along the "Relaxed Skin Tension Lines" (RSTL) as shown in FIG. 12. The objective of this section is to characterize the collagen contraction resulting from a thermal dose applied in dermis by the simulated Sofwave applicator.

Collagen Contraction-Methodology

Collagen contraction in rat tendons resulting from a thermal exposure at 58° C. for up to 15 minutes has been characterized by Lin et al., where the resulting contracted lengths vs. time at 58° C. results are shown in FIG. 13 [FIG. 13 from Lin et al., shows changes in length of rat tail tendon from thermal treatment at 58° C. Error bars represent calculated standard deviations].

Figure 14:
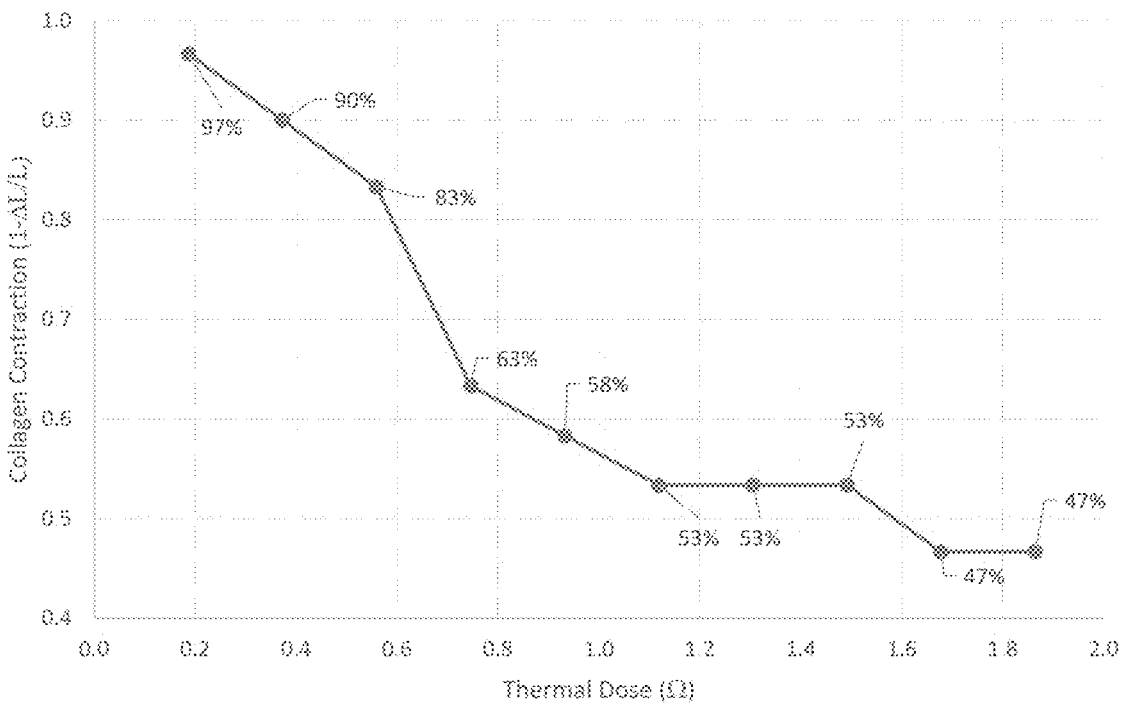
FIG. 14 is a graph showing collagen contraction vs. thermal dose, the bullet numbers represent the residual length after shrinkage.

Since the temperature and time at temperature variables are known, it is possible to calculate the thermal dose received by the collagen fibers using the Arrhenius equation (1), along with the activation energy (E) and frequency factor (A). The collagen shrinkage reported by Lin et al. vs. their associated thermal dose ($\Omega$) is shown in FIG. 14 [FIG. 14 shows Collagen contraction vs. thermal dose. The bullet numbers represent the residual length after shrinkage].

These results were programmed in a commercially available Finite Element Analysis software (Comsol) using a lookup table function to assign a level of collagen contraction to the calculated thermal dose in dermis. Because the original collagen shrinkage data were obtained from animal tendon and not human skin, the absolute values cannot be considered as representative for skin. However, the ratios of shrinkage in 3 orthogonal directions should be fairly representative to indicate directions of shrinkage. These ratios are presented in the following section.

Collagen Contraction—Simulation Results

Figure 15:
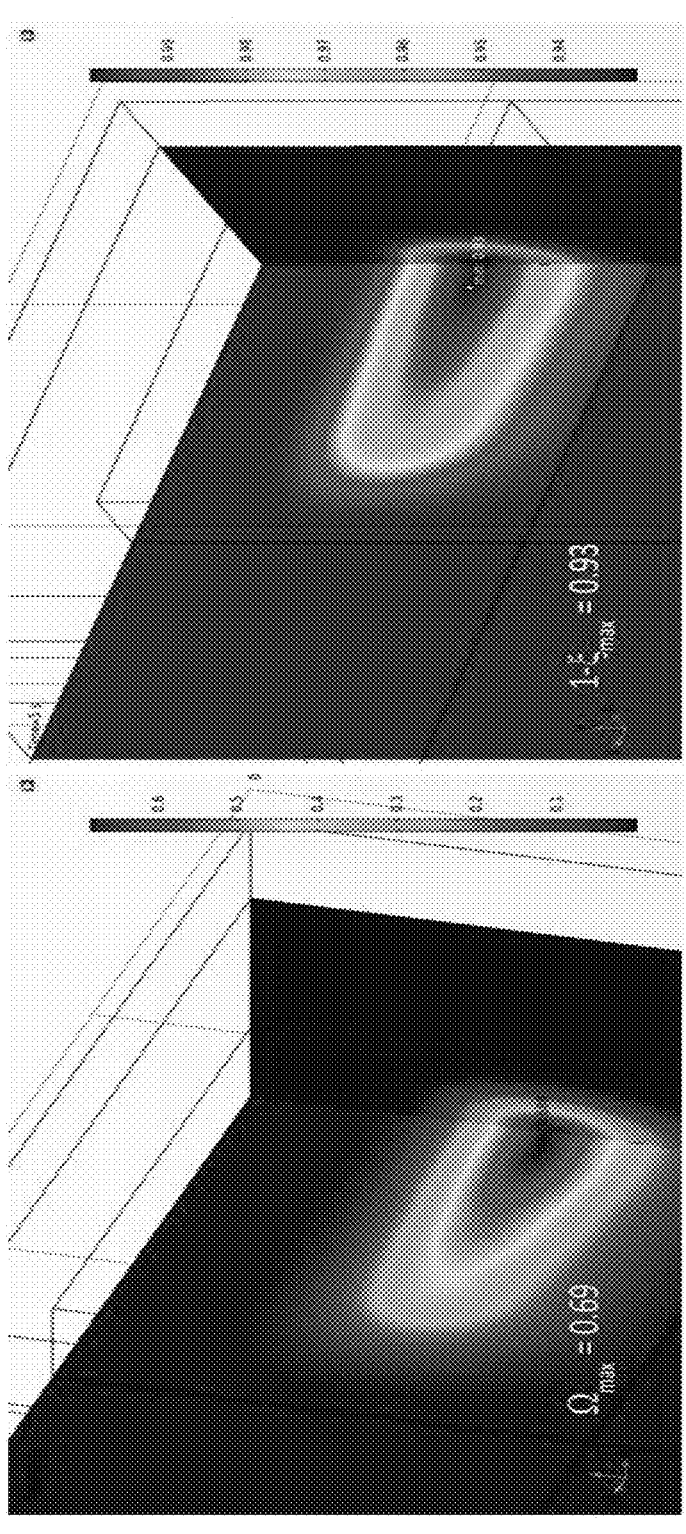
FIG. 15 shows in the left panel a thermal dose in the dermis at 3.6 J, and in the right panel a corresponding collagen deformation.

The collagen deformation ratio ξ was calculated based on the thermal dose Ω obtained in this section. The results obtained with a setting of 3.6 J are shown in FIG. 15 [FIG. 15 shows in the left panel thermal dose in dermis at 3.6 J, and in the right panel-corresponding collagen deformation].

Figure 16:
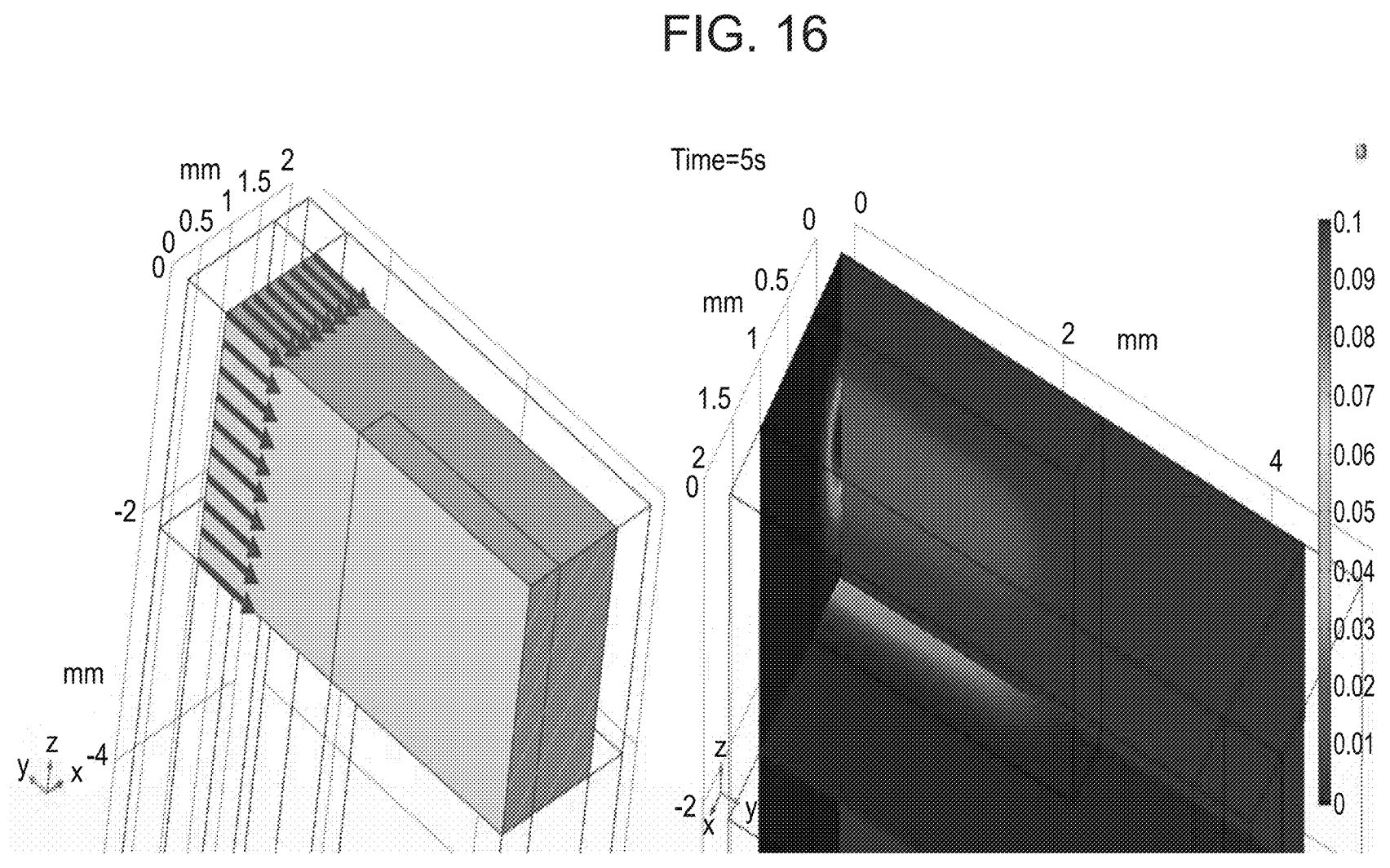

To calculate the absolute collagen shrinkage value, the projection (or line integral) of the collagen deformation field ξ was calculated and plotted in a plane perpendicular to the direction of integration. The line integration method and results are shown in FIG. 16 [FIG. 16 shows in the left panel. The collagen deformation field ξ is integrated in one direction and plotted in a perpendicular plane. In this example, ξ is integrated along the red arrows in the y direction and plotted on the hatched plane in yellow (the xz plane). Right panel—The projection results are shown in the 3 perpendicular planes].

Figure 17:
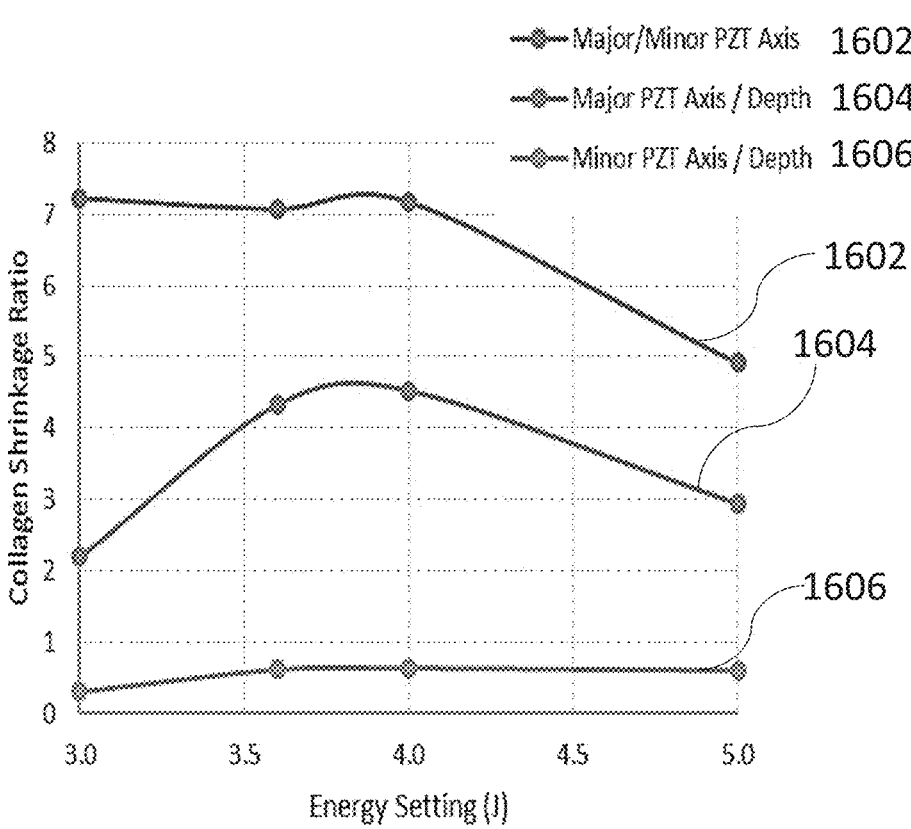
FIG. 17 shows a graph describing collagen shrinkage ratios in 3 orthogonal planes.

From these results, the maximal collagen shrinkage values in the three orthogonal planes were extracted and the ratios between two collagen shrinkage values calculated, which are shown in FIG. 17 for energy settings of 3, 3.6, 4, and 5 J. The main ratio of interest is the "lateral shrinkage ratio" obtained by dividing the collagen shrinkage value along the major PZT axis direction to the one along the minor PZT axis direction (and defined as "Major/Minor PZT axis in the blue curve 1602 of FIG. 17). These two directions are along the skin surface. The results revealed a lateral shrinkage ratio of about 7:1 in a direction, for example a preferred direction, along the main PZT axis between 3 and 4 J, which decreased to about 5:1 at 5 J. Other shrinkage ratios, defined as "Major PZT Axis/Depth" and "Minor PZT Axis/Depth" (as shown with the red curve 1604 and the gray curve 1606 of FIG. 17, respectively) revealed smaller values. For the "Major PZT Axis/Depth" ratio, the ratio started at about 2.1 at 3.0 J before reaching a maximum of about 4.6 at about 3.8 J, to then decrease to a value of about 3.0 at 5.0 J. These ratio values can themselves be used to calculate ratio of ratio values based on the results shown in FIG. 17. For examples using the results obtained at 3.6 J, the "Major/Minor PZT" divided by the "Major PZT Axis/Depth" values would result with a ratio of about 7.0/4.2=1.67.

It can be appreciated that since the collagen shrinkage values in one direction are line integrals of the shrinkage in a direction, increasing the PZT (or other type of transducers) dimension along that direction would result of a larger collagen shrinkage value. Therefore, as an example, a PZT transducer longer than 5 mm along its main (or major) axis, and still 1 mm wide along minor axis would result in "lateral shrinkage ratio" (or Major/Minor PZT Axis in FIG. 17) values larger than the obtained value of about 7:1 reported in this document. Conversely, shorter PZT values along its main axis would result in smaller lateral shrinkage ratio. In some embodiments, as described above, energy is applied to the skin in order to create collagen shrinkage in preferred directions, with a lateral shrinking ratio of at least about 1.5:1, for example a lateral shrinking ratio of at least about 1.7:1, at least about 2:1, at least about 2.5:1, at least about 3:1, at least about 4:1 or any smaller or larger shrinking ratio.

Unlike most energy-based technologies designed to produce relatively isotropic collagen denaturation in dermis, the PZT transducers used in the Sofwave handpiece can produce elongated collagen denaturation along the main PZT axis, as shown in FIG. 14. This is due to the design of the PZT transducer which has an asymmetrical rectangular footprint of 1×5 mm. Because of the collagen denaturation anisotropy, a planned direction, for example a preferred direction, of collagen shrinkage is obtained. This planned direction of shrinkage could be used to maximize shrinkage in one specific direction to obtain a desired effect. In the field of esthetic, the preferred direction of shrinkage could be produced along, or substantially along, the LME lines shown in FIG. 12 in order to at least partially mimic the desired esthetic effects of a face lift. In practice, this would be done by aligning the long PZT axis along, or substantially along, the LME lines for a majority or all the acoustic pulses used to treat the desired facial area. The same concept would apply on the neck where the LME lines generally runs in a vertical manner where the lines are generally perpendicular to the mandibular bone. This technique could be used to improve the appearance or treat wrinkles anywhere on the body such as, for example, the neck, décolleté, knees, arms, abdomen, arms, legs, thighs, legs, to name a few.

Producing thermal injuries to create collagen tightening or shrinkage along a preferred direction could also be useful to tighten collagen-rich tissue such as ligaments in order to treat joins which are prone to dislocation, or to obtain any other desired mechanical tightening effect(s). These joins could include, without limitation, the shoulder, elbow, wrist, fingers, hip, knee, ankle, toc, neck, and/or spine.

Similarly, dysfunctional sphincters prone to improper closing could be targeted. In such applications, the collagen in the tissue surrounding the sphincter would be denatured or shrunk in a direction which would help the sphincter restore its normal function. Generally speaking, this could be achieved by reducing (or shrinking) the perimeter of the sphincter, therefore helping proper sphincter closure. As a consequence, the preferred directions of collagen shrinking would be parallel to the circumference of the sphincter or, in other words, perpendicular, or substantially perpendicular, to the radial lines. These procedures could target the esophageal sphincter for the treatment of GERD or gastric reflux abnormalities, as well as fecal and urinary incontinence, to name a few. The same principle would apply for vaginal tightening where the preferred direction of collagen contraction would be along the vaginal wall in a direction perpendicular to the main vaginal axis.

Esthetic procedures targeting cartilages could also use this technique where a length reduction parallel to the preferred direction of collagen contraction is generally desired. Otoplasty and rhinoplasty would be cited here as non-limiting examples. In addition, cardiac valvuloplasty could be performed and/or enhanced using the procedure aforementioned.

The results of the simulations demonstrate that the Finite Element Analysis model has been validated and capable of predicting the thermal injuries created at different clinically-relevant settings. Based on the results, and in some embodiments clinical results are expected when using settings between about 3 J to about 4.5 J, for example between about 3.5 J to about 4 J, between about 3.5 J to about 4.5 J. Furthermore, the 3D simulation results demonstrated that collagen shrinkage in preferred direction along the main axis of the PZT is achieved, which can be beneficial to create directional skin tightening and partially mimic the effects of a facelift, in one example of application.

It is expected that during the life of a patent maturing from this application many relevant ultrasound transducers will be developed; the scope of the term ultrasound transducer is intended to include all such new technologies a priori.

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for generating directional skin tightening, comprising:
    initiating a directional skin tightening generation process;
    providing at least one alignment indication according to at least one desired vector of skin tightening, for alignment of an energy-emitting transducer on a surface of a skin;
    aligning said at least one energy-emitting transducer on said surface of a skin according to said at least one alignment indication, wherein said at least one energy-emitting transducer comprises at least one ultrasound transducer;
    applying energy by said at least one aligned energy-emitting transducer at two or more locations on a skin surface along said at least one desired vector of skin tightening, wherein said applied energy is used to generate directional skin tightening by forming spaced-apart thermal damage lesions in deep tissue layers of the skin arranged according to the alignment of said at least one energy-emitting transducer and along said at least one desired vector of skin tightening, wherein said directional skin tightening is generated without cutting said skin tissue following said initiating.

2. A method according to claim 1, comprising
    determining said at least one desired vector of skin tightening based on position and/or orientation of at least one skin tension line or at least one wrinkle on said skin surface.

3. A method according to claim 2, wherein said at least one desired vector of skin tightening is oriented at an angle between 45° degrees and 135° degrees relative to said at least one skin tension line or said at least one wrinkle in said skin surface.

4. A method according to claim 3, wherein said at least one skin tension line comprise at least one of, Langer's lines, Cox's lines, Kraissel's lines, Rubin's lines, Straith's lines, Bulacio's lines, and relaxed skin tension lines (RSTL).

5. A method according to claim 1, wherein a minimal distance between two adjacent spaced-apart thermal damage lesions formed along the desired vector, is in a range of 0.1 mm to 20 mm.

6. A method according to claim 1, comprising controlling a depth of said applying according to depth and/or position of nerve tissue along the at least one desired skin tightening vector.

7. A method according to claim 1, wherein said aligning comprises aligning said at least one energy-emitting transducer on said skin surface on said at least one desired skin tightening vector using said at least one alignment indication, and wherein said method comprises repeating said applying in at least two locations on said skin surface positioned along said at least one desired skin tightening vector.

8. A method according to claim 1, wherein said applying comprises moving a skin contacting surface of an ultrasound applicator comprising said at least one energy-emitting transducer between said two locations on said skin surface.

9. A method according to claim 1, wherein said spaced-apart thermal damage lesions are axially arranged along said at least one desired skin tightening vector.

10. A method according to claim 1, wherein said applying said energy comprises heating at least one tissue volume in said deep tissue layers of the skin to a temperature in a range of 50° C. to 80° C., to form at least one thermal damage lesion of said spaced-apart thermal damage lesions.

11. A method according to claim 10, wherein said at least one tissue volume comprises collagen fibers, wherein said applying comprises applying said energy with parameter values sufficient to generate a partial denaturation of said collagen fibers in said at least one tissue volume.

12. A method according to claim 11, wherein said applying comprises applying said energy using at least one energy-emitting transducer having a long axis and a short axis, and wherein said applied energy generates contraction of collagen within said at least one tissue volume along the long axis of the at least one energy-emitting transducer.

13. A method according to claim 11, wherein said applying comprises applying unfocused ultrasound energy or radiofrequency (RF) to said deep tissue layers.

14. A method according to claim 1, wherein said formed spaced-apart thermal damage lesions generate directional skin tightening that at least partly mimics a desired esthetic effect of a facelift or an effect of a mini-facelift in said subject.

15. A method according to claim 1, comprising:
cooling a surface of the skin during said applying to maintain a temperature of said skin surface between 5-40 degrees Celsius.

16. A method for generating directional skin tightening, comprising:
initiating a directional skin tightening generation process;
aligning at least one energy-emitting transducer of an ultrasound applicator on a surface of a skin according to at least one desired vector of skin tightening, wherein said at least one energy-emitting transducer comprises at least one ultrasound transducer;
applying energy by said at least one aligned energy-emitting transducer at two or more locations on a skin surface along said at least one desired vector of skin tightening, wherein said applied energy is used to generate directional skin tightening by forming spaced-apart thermal damage lesions in deep tissue layers of the skin arranged according to the alignment of said at least one energy-emitting transducer and along said at least one desired vector of skin tightening, wherein said directional skin tightening is generated without cutting said skin tissue following said initiating.

17. A method according to claim 16, comprising:
controlling said applicator to prevent damage to the skin surface contacting the applicator.

* * * * *